US010364200B2

(12) United States Patent
Sangar et al.

(10) Patent No.: US 10,364,200 B2
(45) Date of Patent: *Jul. 30, 2019

(54) PROCESSES AND SYSTEMS FOR THE CONVERSION OF ACYCLIC HYDROCARBONS

(71) Applicant: ExxonMobil Chemical Patents Inc., Baytown, TX (US)

(72) Inventors: Neeraj Sangar, League City, TX (US); Larry L. Iaccino, Seabrook, TX (US); Christopher L. Becker, Manhattan, KS (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/892,832

(22) Filed: Feb. 9, 2018

(65) Prior Publication Data
US 2018/0319721 A1    Nov. 8, 2018

Related U.S. Application Data

(60) Provisional application No. 62/500,898, filed on May 3, 2017.

(51) Int. Cl.
*C07C 5/333* (2006.01)
*B01J 8/24* (2006.01)
*C07C 5/373* (2006.01)

(52) U.S. Cl.
CPC .............. *C07C 5/3337* (2013.01); *B01J 8/24* (2013.01); *C07C 5/373* (2013.01);
(Continued)

(58) Field of Classification Search
CPC ........................................ C07C 5/333–5/3337
See application file for complete search history.

(56) References Cited

U.S. PATENT DOCUMENTS 2,344,330 A   3/1944   Sturgeon
2,435,404 A   3/1948   Hetzel et al.
(Continued)

FOREIGN PATENT DOCUMENTS

WO    2017/078892 A    5/2017
WO    2017/078905      5/2017

OTHER PUBLICATIONS

Vora, B.V., "Development of Dehydrogenation Catalysts and Processes," Topics in Catalysis, vol. 55, pp. 1297-1308, 2012.
(Continued)

*Primary Examiner* — Philip Y Louie
*Assistant Examiner* — Alyssa L Cepluch
(74) *Attorney, Agent, or Firm* — Kevin M. Faulkner

(57) ABSTRACT

This invention relates to processes and systems for converting acyclic hydrocarbons to alkenes, cyclic hydrocarbons and/or aromatics, for example converting acyclic $C_5$ hydrocarbons to cyclopentadiene in a reactor system. The process includes contacting a feedstock comprising acyclic hydrocarbons with a catalyst material in at least one reaction zone to convert at least a portion of the acyclic hydrocarbons to a first effluent comprising alkenes, cyclic hydrocarbons and/or aromatics. A co-feed comprising $H_2$, $C_1$-$C_4$ alkanes and/or $C_1$-$C_4$ alkenes may also be provided to the at least one reaction zone.

19 Claims, 1 Drawing Sheet

(52) U.S. Cl.
CPC .............. *B01J 2208/00752* (2013.01); *B01J 2208/00761* (2013.01); *B01J 2208/00991* (2013.01); *C07C 2529/44* (2013.01); *C07C 2601/10* (2017.05)

(56) References Cited

U.S. PATENT DOCUMENTS

| | | | |
|---|---|---|---|
| 2,438,398 | A | 3/1948 | Kennedy et al. |
| 2,438,399 | A | 3/1948 | Kennedy et al. |
| 2,438,400 | A | 3/1948 | Hetzel et al. |
| 2,438,401 | A | 3/1948 | Kennedy et al. |
| 2,438,402 | A | 3/1948 | Kennedy et al. |
| 2,438,403 | A * | 3/1948 | Kennedy .................. B01J 23/70 585/369 |
| 2,893,849 | A | 7/1959 | Krebs |
| 2,982,798 | A | 5/1961 | Hachmuth et al. |
| 3,953,368 | A | 4/1976 | Sinfelt |
| 5,030,338 | A * | 7/1991 | Harandi .................. B01J 29/90 208/135 |
| 5,192,728 | A | 3/1993 | Dessau et al. |
| 5,254,787 | A | 10/1993 | Dessau |
| 5,284,986 | A | 2/1994 | Dessau |
| 5,633,421 | A | 5/1997 | Iezzi et al. |
| 7,728,186 | B2 * | 6/2010 | Iaccino .................... C07C 2/76 585/407 |
| 9,303,217 | B2 | 4/2016 | Ma et al. |
| 2012/0022310 | A1 * | 1/2012 | Schneider ................. C07C 2/76 585/415 |
| 2016/0152528 | A1 | 6/2016 | Petters et al. |
| 2016/0362351 | A1 * | 12/2016 | Nagaki ..................... C07C 2/76 |
| 2017/0121251 | A1 * | 5/2017 | Iaccino .................... C07C 5/373 |

OTHER PUBLICATIONS

Bricker; J.C., "Advanced Catalytic Dehydrogenation Technologies for Production of Olefins ," Topics in Catalysis, vol. 55, pp. 1309-1314, 2012.

Kanazirev, V., et al., "Conversion of C8 aromatics and n-pentane over Ga2O3/H-ZSM-5 mechanicaliy mixed catalysts," Catalysis Letters, vol. 9, pp. 35-42, 1991.

Xu, Y., et al. "Methane activation without using oxidants over Mo/HZSM-5 zeolite catalysts," Catalysis Letters, vol. 30, pp. 135-149, 1994.

Kennedy, R.M., et al., "Formation of Cyclopentadiene from 1,3-Pentadiene," Industrial & Engineering Chemistry, vol. 42, pp. 547-552, 1950.

Fel'dblyum, V.S., et al. in "Cyclization and dehydrocyclization of C5 hydrocarbons over platinum nanocatalysts and in the presence of hydrogen sulfide," Doklady Chemistry, vol. 424, pp. 27-30, 2009.

Marcinkowski, T.E., "Isomerization and Dehydrogenation of 1,3-Pentadiene"; University of Central Florida, 1979.

López, C.M., et al. "n-Pentane Hydroisomerization on Pt Containing HZSM-5, HBEA, and SAPO-11," Catalysis Letters, vol. 122, pp. 267-273, 2008.

Li, X., et al. in "Catalytic dehydroisomerization of n-alkanes to isoalkenes," Journal of Catalysis, vol. 255, pp. 134-137, 2008.

* cited by examiner

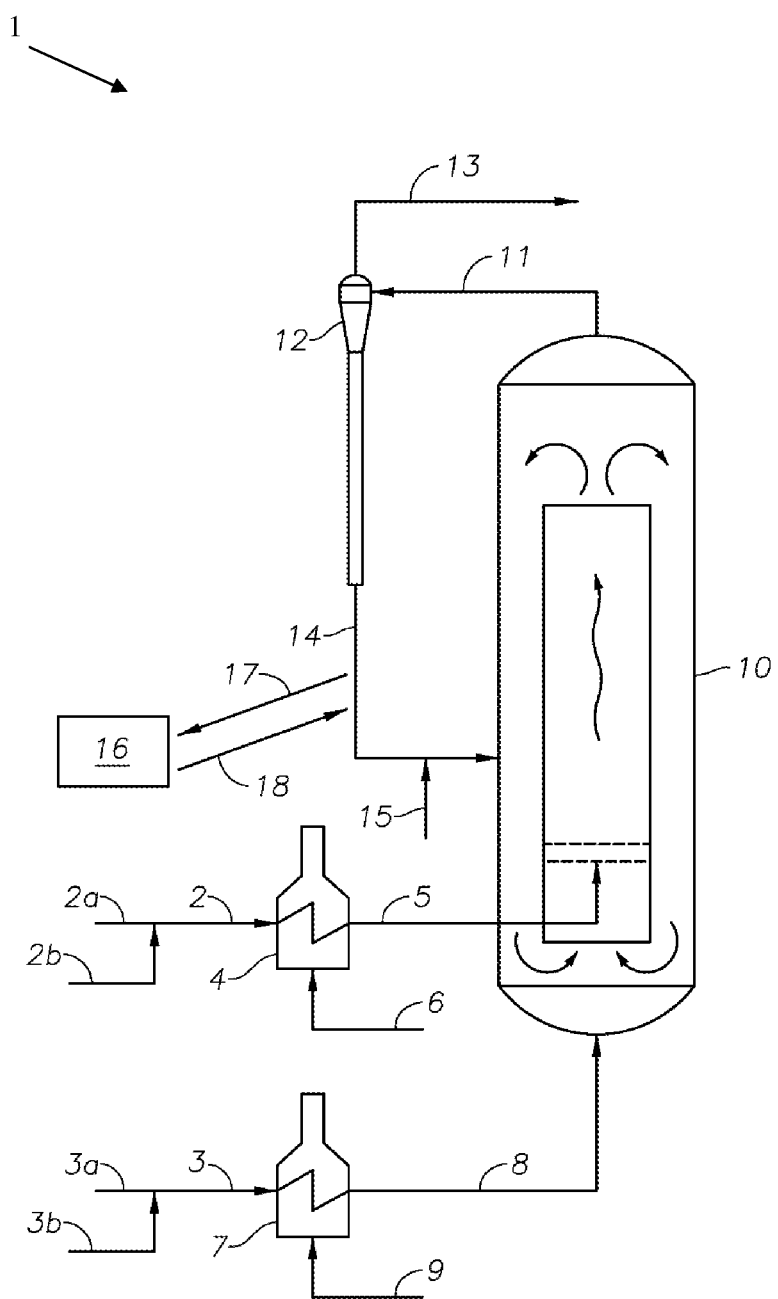

PROCESSES AND SYSTEMS FOR THE CONVERSION OF ACYCLIC HYDROCARBONS

CROSS-REFERENCE TO RELATED APPLICATION

This application claims priority to U.S. Provisional Application Ser. No. 62/500,898, filed May 3, 2017, the disclosures of which is incorporated herein by reference.

FIELD OF THE INVENTION

This invention relates to processes and reactor systems for the conversion of acyclic hydrocarbons to alkenes, cyclic hydrocarbons and/or aromatics.

BACKGROUND OF THE INVENTION

Cyclic hydrocarbons, alkenes and aromatics, such as cyclopentadiene ("CPD") and its dimer dicyclopentadiene ("DCPD"), ethylene, propylene, and benzene, are highly desired raw materials used throughout the chemical industry in a wide range of products, for example, polymeric materials, polyester resins, synthetic rubbers, solvents, fuels, fuel additives, etc. These compounds are typically derived from various streams produced during refinery processing of petroleum. In particular, CPD is currently a minor byproduct of liquid feed steam cracking (e.g., naphtha, and heavier feed). As existing and new steam cracking facilities shift to lighter feeds, less CPD is produced while demand for CPD is rising. High cost due to supply limitations impacts the potential end product use of CPD in polymers. More CPD-based polymer product could be produced if additional CPD could be produced at unconstrained rates and preferably at a cost lower than recovery from steam cracking. When producing CPD, co-production of other cyclic $C_5$ compounds is also desirable. Cyclopentane and cyclopentene can have high value as solvents while cyclopentene may be used as a comonomer to produce polymers and as a starting material for other high value chemicals.

It would be advantageous to be able to produce these cyclic hydrocarbons, alkenes and aromatics, including CPD, propylene, ethylene, and benzene, as the primary product from plentiful hydrocarbon feedstock. Specifically, when producing CPD, it is also desirable to minimize production of light ($C_{4-}$) byproducts. While a feedstock composed of lower hydrogen content (e.g., cyclics, alkenes, and dialkenes) could be preferred because the reaction endotherm is reduced and thermodynamic constraints on conversion are improved, non-saturates are more expensive than saturate feedstock. Linear hydrocarbon skeletal structure is preferred over branched hydrocarbon skeletal structures due to both reaction chemistry and the lower value of linear hydrocarbon relative to branched hydrocarbon (due to octane differences). Further, an abundance of hydrocarbons, such as $C_5$ hydrocarbons, are available from unconventional gas and shale oil, as well as reduced use in motor fuels due to stringent environmental regulations. Various hydrocarbon feedstocks, such as $C_5$ feedstock, may also be derived from bio-feeds.

Various catalytic dehydrogenation technologies are currently used to produce mono- and di-olefins from $C_3$ and $C_4$ alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes," Topics in Catalysis, vol. 55, pp. 1297-1308, 2012; and J. C. Bricker, "Advanced Catalytic Dehydrogenation Technologies for Production of Olefins," Topics in Catalysis, vol. 55, pp. 1309-1314, 2012.

Still another common process uses Pt/Sn supported on Zn and/or Ca aluminate to dehydrogenate propane. While these processes are successful in dehydrogenating alkanes, they do not perform cyclization, which is critical to producing CPD. Pt—Sn/alumina and Pt—Sn/aluminate catalysts exhibit moderate conversion of n-pentane, but such catalyst have poor selectivity and yield to cyclic $C_5$ products.

Pt supported on chlorided alumina catalysts are used to reform low octane naphtha to aromatics such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing $C_6$ and higher alkanes to form $C_6$ aromatic rings, they are less effective in converting acyclic $C_5$s to cyclic $C_5$s. These Pt supported on chlorided alumina catalysts exhibit low yields of cyclic $C_5$ and exhibit deactivation within the first two hours of time on stream. Cyclization of $C_6$ and $C_7$ alkanes is aided by the formation of an aromatic ring, which does not occur in $C_5$ cyclization. This effect may be due in part to the much higher heat of formation for CPD, a cyclic $C_5$, as compared to benzene, a cyclic $C_6$, and toluene, a cyclic $C_7$. This is also exhibited by Pt/Ir and Pt/Sn supported on chlorided alumina. Although these alumina catalysts perform both dehydrogenation and cyclization of $C_{6+}$ species to form $C_6$ aromatic rings, a different catalyst will be needed to convert acyclic $C_5$ to cyclic $C_5$.

Ga-containing ZSM-5 catalysts are used in a process to produce aromatics from light paraffins. A study by Kanazirev et al. showed n-pentane is readily converted over $Ga_2O_3$/H-ZSM-5. See Kanazirev Price et al., "Conversion of $C_8$ aromatics and n-pentane over $Ga_2O_3$/H-ZSM-5 mechanically mixed catalysts," Catalysis Letters, vol. 9, pp. 35-42, 1991. No production of cyclic $C_5$ was reported while upwards of 6 wt % aromatics were produced at 440° C. and 1.8 $hr^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic $C_5$ and high yield to cracking products. This shows that ZSM-5-based catalysts can convert paraffins to a $C_6$ ring, but not necessarily to produce a $C_5$ ring.

U.S. Pat. No. 5,254,787 (Dessau) introduced the NU-87 catalyst used in the dehydrogenation of paraffins. This catalyst was shown to dehydrogenate $C_2$-$C_{6+}$ to produce their unsaturated analogs. A distinction between $C_{2-5}$ and $C_{6+}$ alkanes was made explicit in this patent: dehydrogenation of $C_{2-5}$ alkanes produced linear or branched mono-olefins or di-olefins, whereas dehydrogenation of $C_{6+}$ alkanes yielded aromatics. U.S. Pat. No. 5,192,728 (Dessau) involves similar chemistry, but with a tin-containing crystalline microporous material. As with the NU-87 catalyst, $C_5$ dehydrogenation was only shown to produce linear or branched, mono-olefins or di-olefins and not CPD.

U.S. Pat. No. 5,284,986 (Dessau) introduced a dual-stage process for the production of cyclopentane and cyclopentene from n-pentane. An example was conducted wherein the first stage involved dehydrogenation and dehydrocyclization of n-pentane to a mix of paraffins, mono-olefins and di-olefins, and naphthenes over a Pt/Sn-ZSM-5 catalyst. This mixture was then introduced to a second-stage reactor consisting of Pd/Sn-ZSM-5 catalyst where dienes, especially CPD, were converted to olefins and saturates. Cyclopentene was the desired product in this process, whereas CPD was an unwanted byproduct.

U.S. Pat. Nos. 2,438,398; 2,438,399; 2,438,400; 2,438,401; 2,438,402; 2,438,403; and U.S. Pat. No. 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," *Industrial & Engineering Chemistry*, vol. 42, pp. 547-552, 1950.

Fel'dblyum et al. in "Cyclization and dehydrocyclization of $C_5$ hydrocarbons over platinum nanocatalysts and in the presence of hydrogen sulfide," *Doklady Chemistry*, vol. 424, pp. 27-30, 2009, reported production of CPD from 1,3-pentadiene, n-pentene, and an n-pentane. Yields to CPD were as high as 53%, 35%, and 21% for the conversion of 1,3-pentadiene, n-pentene, and an n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over $Pt—Sn/SiO_2$, but with poor selectivity and yield to cyclic $C_5$ products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3,-pentadiene with 80% selectivity to CPD with $H_2S$ at 700° C. High temperature, limited feedstock, and potential of products containing sulfur that would later need scrubbing make this process undesirable.

Lopez et al. in "n-Pentane Hydroisomerization on Pt Containing HZSM-5, HBEA, and SAPO-11," *Catalysis Letters*, vol. 122, pp. 267-273, 2008, studied reactions of n-pentane on Pt-containing zeolites including H-ZSM-5. At intermediate temperatures (250° C.–400° C.), they reported efficient hydroisomerization of n-pentane on the Pt-zeolites with no discussion of cyclopentene formation. It is desirable to avoid this deleterious chemistry as branched $C_5$ do not produce cyclic $C_5$ as efficiently as linear $C_5$, as discussed above.

Li et al. in "Catalytic dehydroisomerization of n-alkanes to isoalkenes," *Journal of Catalysis*, vol. 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic $C_5$ were produced and undesirable skeletal isomerization occurred.

U.S. Pat. No. 5,633,421 discloses a process for dehydrogenating $C_2$-$C_5$ paraffins to obtain corresponding olefins. Similarly, U.S. Pat. No. 2,982,798 discloses a process for dehydrogenating an aliphatic hydrocarbon containing 3 to 6, inclusive, carbon atoms. However, neither U.S. Pat. No. 5,633,421 nor U.S. Pat. No. 2,982,798 disclose production of CPD from acyclic $C_5$ hydrocarbons, which are desirable as feedstock because they are plentiful and low cost.

Further, on-purpose production of CPD, propylene, ethylene, and benzene is accomplished via endothermic reactions. Engineering process and reactor design for catalyst driven endothermic reactions present many challenges. For example, maintaining high temperatures required for the reactions, including transferring a large amount of heat to a catalyst, can be difficult. Production of CPD is especially difficult amongst endothermic processes because it is favored by low pressure and high temperature, but competing reactions such as cracking of n-pentane and other $C_5$ hydrocarbons can occur at relatively low temperature (e.g., 450° C.–500° C.).

Additional challenges may include loss of catalyst activity due to coking during the process and further processing needed to remove coke from the catalyst, and the inability to use oxygen-containing gas to directly provide the heat input necessary to counter the endothermic nature of the reaction without damaging the catalyst. Moreover, non-uniform catalyst aging can also occur, which can impact resulting product selectivity and catalyst life.

Furthermore, challenges exist in reactor design, especially with respect to material selection, since the reactions are carried out at higher temperatures and highly carburizing conditions. Metal alloys can potentially undergo carburization (resulting in loss in mechanical properties) as well as metal dusting (resulting in loss of metal via formation of metastable carbides) under the desired reaction conditions. Thus, given the need for large heat input to drive the reaction, metallic heat-transfer surfaces exposed to the reaction mixture need to be capable of resisting attack via carburization/metal dusting.

Hence, there remains a need for a process to convert acyclic hydrocarbons to alkenes, cyclic hydrocarbons and aromatics, particularly acyclic $C_5$ hydrocarbon to CPD, preferably at commercial rates and conditions. Further, there is a need for a catalytic process targeted for the production of CPD, which generates CPD in high yield from plentiful $C_5$ feedstocks without excessive production of $C_{4-}$ cracked products and with acceptable catalyst aging properties. Additionally, there is a need for processes and systems for on-purpose production of CPD, propylene, ethylene, and benzene from acyclic hydrocarbons, which addresses the above-described challenges.

SUMMARY OF THE INVENTION

In one aspect, this invention relates to a process for converting acyclic hydrocarbons to alkenes, cyclic hydrocarbons and/or aromatics in a reactor system, wherein the process comprises: contacting a feedstock comprising acyclic hydrocarbons and optionally hydrogen with a catalyst material in at least one reaction zone under reaction conditions to convert at least a portion of the acyclic hydrocarbons to a first effluent comprising alkenes, cyclic hydrocarbons and/or aromatics, wherein the feedstock enters the at least one reaction zone at a temperature of about 300° C. to about 700° C.; and providing a co-feed comprising hydrogen, alkanes (e.g., $C_1$-$C_4$ alkanes) and/or alkenes (e.g., $C_1$-$C_4$ alkenes) at a temperature of about 600° C. to about 1100° C. to heat the at least one reaction zone, wherein the feedstock and the co-feed are provided to the at least one reaction zone at different locations via different inlets. The feedstock and the co-feed may be provided to the at least one reaction zone simultaneously or not. Preferably, the feedstock and the co-feed are provided to the at least one reaction zone simultaneously.

In another aspect, this invention also relates to a reaction system for converting acyclic hydrocarbons to alkenes, cyclic hydrocarbons and/or aromatics, wherein the reaction system comprises a feedstock stream comprising acyclic hydrocarbons and optionally hydrogen having a temperature of about 300° C. to about 700° C.; a co-feed stream comprising hydrogen, alkanes (e.g., $C_1$-$C_4$ alkanes) and/or alkenes (e.g., $C_1$-$C_4$ alkenes) having a temperature of about 600° C. to about 1100° C.; an effluent stream comprising alkenes, cyclic hydrocarbons and/or aromatics; a separated catalyst material stream; and a substantially catalyst-free effluent stream; at least one reactor operated under reaction conditions to convert at least a portion of the acyclic hydrocarbons to alkenes, cyclic hydrocarbons and/or aromatics, wherein the at least one reactor comprises: a feedstock stream inlet; a co-feed stream inlet; a catalyst material stream inlet; and an effluent stream outlet; and a separator for separating catalyst material from the effluent stream to produce the separated catalyst material stream and the second effluent stream, wherein the separator is in fluid connection with the at least one reactor and comprises an effluent stream inlet, a separated catalyst material stream outlet and a substantially catalyst-free effluent stream outlet.

BRIEF DESCRIPTION OF THE FIGURES

The FIGURE is a diagram of a reactor system according to an embodiment of the invention.

DETAILED DESCRIPTION OF THE INVENTION

All numerical values within the detailed description and the claims herein are modified by "about" or "approximately" the indicated value, and take into account experimental error and variations that would be expected by a person having ordinary skill in the art. Unless otherwise indicated, room temperature is about 23° C.

I. Definitions

To facilitate an understanding of the present invention, a number of terms and phrases are defined below.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A", and "B."

As used herein, the term "about" refers to a range of values of plus or minus 10% of a specified value. For example, the phrase "about 200" includes plus or minus 10% of 200, or from 180 to 220.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. The term "$C_n$" means hydrocarbon(s) having n carbon atom(s) per molecule, wherein n is a positive integer.

As used herein, the term "light hydrocarbon" means light paraffinic and/or olefinic hydrocarbons comprised substantially of hydrogen and carbon only and has one to no more than 4 carbon atoms.

The term "saturates" includes, but is not limited to, alkanes and cycloalkanes.

The term "non-saturates" includes, but is not limited to, alkenes, dialkenes, alkynes, cyclo-alkenes, and cyclo-dialkenes.

The term "cyclic hydrocarbon" denotes groups such as the cyclopropane, cyclopropene, cyclobutane, cyclobutadiene etc., and substituted analogues of these structures. These cyclic hydrocarbons can be single- or multi-ring structures. Preferably, the term "cyclic hydrocarbon" refers to non-aromatics.

The term "cyclics $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclics" includes, but is not limited to, linear and branched saturates and non-saturates.

The term "alkane" refers to non-aromatic saturated hydrocarbons with the general formula $C_nH_{(2n+2)}$, where n is 1 or greater. An alkane may be straight chained or branched. Examples of alkanes include, but are not limited to methane, ethane, propane, butane, pentane, hexane, heptane and octane. "Alkane" is intended to embrace all structural isomeric forms of an alkane. For example, butane encompasses n-butane and isobutane; pentane encompasses n-pentane, isopentane and neopentane.

The term "alkene," alternatively referred to as "olefin," refers to a branched or unbranched unsaturated hydrocarbon having one or more carbon-carbon double bonds. A simple alkene comprises the general formula $C_nH_{2n}$, where n is 2 or greater. Examples of alkenes include, but are not limited to ethylene, propylene, butylene, pentene, hexene and heptene. "Alkene" is intended to embrace all structural isomeric forms of an alkene. For example, butylene encompasses but-1-ene, (Z)-but-2-ene, etc.

The term "aromatic" means a planar cyclic hydrocarbyl with conjugated double bonds, such as benzene. As used herein, the term aromatic encompasses compounds containing one or more aromatic rings, including, but not limited to, benzene, toluene, and xylene, and polynuclear aromatics (PNAs), which include naphthalene, anthracene, chrysene, and their alkylated versions. The term "$C_{6+}$ aromatics" includes compounds based upon an aromatic ring having six or more ring atoms, including, but not limited to, benzene, toluene, and xylene, and polynuclear aromatics (PNAs), which include naphthalene, anthracene, chrysene, and their alkylated versions.

The term "BTX" includes, but is not limited to, a mixture of benzene, toluene, and xylene (ortho and/or meta and/or para).

The term "coke" includes, but is not limited to, a low hydrogen content hydrocarbon that is adsorbed on the catalyst composition.

The term "$C_{n+}$" means hydrocarbon(s) having at least n carbon atom(s) per molecule.

The term "$C_{n-}$" means hydrocarbon(s) having no more than n carbon atom(s) per molecule.

The term "$C_5$ feedstock" includes a feedstock containing n-pentane, such as a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27 (1985), unless otherwise specified.

The term "Group 10 metal" means an element in Group 10 of the Periodic Table and includes, but is not limited to, Ni, Pd, and Pt, and a mixture of two or more thereof.

The term "Group 11 metal" means an element in Group 11 of the Periodic Table and includes, but is not limited to, Cu, Ag, Au, and a mixture of two or more thereof.

The term "Group 1 alkali metal" means an element in Group 1 of the Periodic Table and includes, but is not limited to, Li, Na, K, Rb, Cs, and a mixture of two or more thereof, and excludes hydrogen.

The term "Group 2 alkaline earth metal" means an element in Group 2 of the Periodic Table and includes, but is not limited to, Be, Mg, Ca, Sr, Ba, and a mixture of two or more thereof.

The term "rare earth metal" means an element in the Lanthanide series of the Periodic Table, as well as scandium and yttrium. The term rare earth metal includes, but is not limited to, lanthanum, praseodymium, neodymium, cerium, yttrium, and a mixture of two or more thereof.

The term "oxygen" includes air, $O_2$, $H_2O$, CO, and $CO_2$.

The term "constraint index" is defined in U.S. Pat. Nos. 3,972,832 and 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms, which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding of at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "microporous crystalline material" or "zeolite."

As used herein, the term "selectivity" means the moles of carbon in the respective cyclic $C_5$, CPD, $C_1$, and $C_{2-4}$ formed divided by total moles of carbon in the pentane converted. For example, the term "carbon selectivity to cyclic $C_5$ of at least 30%" means that at least 30 moles of carbon in the cyclic $C_5$ is formed per 100 moles of carbon in the pentane converted.

As used herein, the term "conversion" means the moles of carbon in the acyclic $C_5$ feedstock that is converted to a product. The phrase "a conversion of at least 70% of said acyclic $C_5$ feedstock to said product" means that at least 70% of the moles of said acyclic $C_5$ feedstock was converted to a product.

As used herein, the term "Alpha Value" is used as a measure of the cracking activity of a catalyst and is described in U.S. Pat. No. 3,354,078 and in the Journal of Catalysis, Vol. 4, p. 527 (1965); Vol. 6, p. 278, (1966) and Vol. 61, p. 395, (1980), each incorporated herein by reference. The experimental conditions of the test used herein included a constant temperature of 538° C. and a variable flow rate as described in detail in the Journal of Catalysis, Vol. 61, p. 395, (1980).

As used herein, the term "reactor system" refers to a system including one or more reactors and all necessary and optional equipment used in the production of cyclopentadiene.

As used herein, the term "reactor" refers to any vessel(s) in which a chemical reaction occurs. Reactor includes both distinct reactors, as well as reaction zones within a single reactor apparatus and, as applicable, reactions zones across multiple reactors. In other words, and as is common, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or a diabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention. As used herein, the term "diabatic" refers to a reactor/reaction zone to which heat is supplied by a means in addition to that provided by the flowing process fluid.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where $U_{mf}$ is minimum fluidizing velocity, $U_{mb}$ is minimum bubbling velocity, $U_c$ is the velocity at which fluctuation in pressure peaks, and tr is transport velocity. These different fluidization regimes have been described in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010, which are incorporated by reference.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$, in at least a portion of the reaction zone, and/or operating at a velocity higher than the minimum fluidization velocity while maintaining a gradient in gas and/or solid property (such as, temperature, gas, or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein, the term "cascaded fluid-beds" means a series arrangement of individual fluid-beds such that there can be a gradient in gas and/or solid property (such as, temperature, gas, or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor. Additionally, a fluidized bed reactor may be a "captive fluidized bed reactor" wherein solids (e.g., catalyst material) may circulate between reaction zones but are not circulated, on a continuous flow basis, between the reactor and a separate vessel (e.g., to perform re-heating and/or regeneration). Solids (e.g., catalyst material) may be withdrawn from the reactor and returned (along with any fresh solids addition) to the reactor after batchwise regeneration performed in a separate vessel. Also, presence of an external cyclone (or any similar device to separate solids from the reactor effluent stream) and its return standpipe is considered part of the captive fluidized bed reactor, i.e., does not constitute a separate vessel for the purpose of defining a captive fluidized bed reactor.

As used herein, the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010. A fluidized bed reactor, such as a circulating fluidized bed reactor, may be operated as a riser reactor. "Average diameter" for particles in the range of 1 to 3500 μm is determined using a Mastersizer™ 3000 available from Malvern Instruments, Ltd., Worcestershire, England. Unless otherwise stated, particle size is determined at D50. D50 is the value of the particle diameter at 50% in the cumulative distribution. For example, if D50=5.8 um, then 50% of the particles in the sample are equal to or larger than 5.8 um and 50% are smaller than 5.8 um. (In contrast, if D90=5.8 um, then 10% of the particles in the sample are larger than 5.8 um and 90% are smaller than 5.8 um.) "Average diameter" for particles in the range of 3 mm to 50 mm is determined using a micrometer on a representative sample of 100 particles.

For purposes of the invention, 1 psi is equivalent to 6.895 kPa. Particularly, 1 psia is equivalent to 1 kPa absolute (kPa-a). Likewise, 1 psig is equivalent to 6.895 kPa gauge (kPa-g).

II. Acyclic Hydrocarbon Conversion Process

In a first aspect, this invention relates to a process for converting acyclic hydrocarbons to alkenes, cyclic hydrocarbons and/or aromatics in a reactor system. The process may comprise contacting a feedstock comprising acyclic hydrocarbons and optionally hydrogen with a catalyst material in at least one reaction zone under reaction conditions to convert at least a portion of the acyclic hydrocarbons to a first effluent comprising alkenes, cyclic hydrocarbons and/or aromatics and providing a co-feed comprising hydrogen, alkanes (e.g., $C_1$-$C_4$ alkanes) and/or alkenes (e.g., $C_1$-$C_4$ alkenes) at a temperature of about 600° C. to about 1100° C. to heat the at least one reaction zone. In various aspects, the feedstock enters the at least one reaction zone at a temperature of about 300° C. to about 700° C. Additionally, the feedstock and the co-feed may be provided to the at least one reaction zone at different locations via different inlets.

In one or more embodiments, this invention relates to a process for conversion of an acyclic $C_5$ feedstock to a product comprising cyclic $C_5$ compounds (e.g., cyclopentadiene). The process comprises contacting said feedstock and, optionally, hydrogen under acyclic $C_5$ conversion conditions in the presence of one or more catalyst compositions, including but not limited to the catalyst compositions described herein, and providing a co-feed as described herein to form said product.

In one or more embodiments, the product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. In one or more embodiments, the cyclic $C_5$ compounds comprise at least about 20 wt %, or 30 wt %, or 40 wt %, or 70 wt % cyclopentadiene, or in the range of from about 10 wt % to about 80 wt %, alternately 20 wt % to 70 wt %.

In one or more embodiments, the acyclic $C_5$ conversion conditions include at least a temperature, an n-pentane partial pressure, and a weight hourly space velocity (WHSV). The temperature is in the range of about 400° C. to about 700° C., or in the range from about 450° C. to about 650° C., preferably, in the range from about 500° C. to about 600° C. The n-pentane partial pressure is in the range of about 3 to about 100 psia at the reactor inlet, or in the range from about 3 to about 50 psia, preferably, in the range from about 3 psia to about 20 psia. The weight hourly space velocity is in the range from about 1 to about 50 $hr^{-1}$, or in the range from about 1 to about 20 $hr^{-1}$. Such conditions include a molar ratio of the optional hydrogen co-feed to the acyclic $C_5$ feedstock in the range of about 0 to 3, or in the range from about 1 to about 2. Such conditions may also include co-feed $C_1$-$C_4$ hydrocarbons with the acyclic $C_5$ feed.

In one or more embodiments, this invention relates to a process for conversion of n-pentane to cyclopentadiene comprising the steps of contacting n-pentane and, optionally, hydrogen (if present, typically $H_2$ is present at a ratio to n-pentane of 0.01 to 3.0) with one or more catalyst compositions, including but not limited to the catalyst compositions described herein, and providing a co-feed as described herein to form cyclopentadiene at a temperature of 400° C. to 700° C., an n-pentane partial pressure of 3 to about 100 psia at the reactor inlet, and a weight hourly space velocity of 1 to about 50 $hr^{-1}$.

A. Feedstock and Co-Feed

In the process, a feedstock comprising acyclic hydrocarbons, preferably acyclic $C_2$-$C_{10}$ hydrocarbons are provided to a reactor system comprising a catalyst material and an inert material. Acyclic $C_2$-$C_{10}$ hydrocarbons include, but are not limited to alkanes (e.g., ethane, propane, butane, pentane, hexane, etc.), alkenes (e.g., ethylene, propylene, butylene, etc.), alkynes (e.g., ethyne, propyne, 1-butyne, 2-butyne, etc.), dialkenes (e.g., 1,2-propadiene, 1,3-butadiene, 1,3-pentadiene, etc.) and combinations thereof. An acyclic $C_2$-$C_{10}$ hydrocarbon feedstock, useful herein, is obtainable from crude oil or natural gas condensate. Optionally, hydrogen may be present in the feedstock as well. The molar ratio of optional hydrogen to acyclic hydrocarbon is preferably between about 0 to about 3, or in the range of about 1 to about 2. Hydrogen may be included in the feedstock in order to minimize production of coke material on the particulate material and/or to fluidize the particulate material in the at least one reaction zone.

Preferably, in one or more embodiments, the acyclic $C_5$ feedstock comprises at least about 50 wt %, or 60 wt %, or 75 wt %, or 90 wt % acyclic hydrocarbons, or in the range from about 50 wt % to about 100 wt % n-pentane. Preferably, an amount of the acyclic hydrocarbons in the feedstock converted to alkenes (e.g., propylene), cyclic hydrocarbons (e.g., cyclopentadiene) and/or aromatics (e.g., benzene) is ≥ about 5.0 wt %, ≥ about 10.0 wt %, ≥ about 20.0 wt %, ≥ about 30.0 wt %, ≥ about 40.0 wt %, ≥ about 50.0 wt %, ≥ about 60.0 wt %, ≥ about 70.0 wt %, ≥ about 80.0 wt %, or ≥ about 90.0 wt %.

In various aspects, the feedstock may preferably be an acyclic $C_5$ feedstock and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

In one or more embodiments, the acyclic $C_5$ feedstock useful in the process of this invention comprises pentane, pentene, pentadiene and mixtures of two or more thereof. Preferably, in one or more embodiments, the acyclic $C_5$ feedstock comprises at least about 50 wt %, or 60 wt %, or 75 wt %, or 90 wt % n-pentane, or in the range from about 50 wt % to about 100 wt % n-pentane.

The acyclic hydrocarbon feedstock optionally does not comprise $C_6$ aromatic compounds, such as benzene. Preferably, $C_6$ aromatic compounds are present at less than 5 wt %, preferably less than 1 wt %, preferably less than 0.01 wt %, and preferably at zero wt %. Additionally, or alternatively, the acyclic hydrocarbon feedstock optionally does not comprise benzene, toluene, or xylene (ortho, meta, or para). Preferably, any benzene, toluene, or xylene (ortho, meta, or para) compounds are present at less than 5 wt %, preferably less than 1 wt %, preferably less than 0.01 wt %, and preferably at zero wt %.

The acyclic hydrocarbon feedstock optionally does not comprise $C_{6+}$ aromatic compounds. Preferably, $C_{6+}$ aromatic compounds are present at less than 5 wt %, preferably less than 1 wt %, preferably less than 0.01 wt %, and preferably at zero wt %.

Preferably, an amount of the $C_5$ hydrocarbons (e.g., acyclic $C_5$ hydrocarbons) in the feedstock converted to cyclopentadiene is ≥ about 5.0 wt %, ≥ about 10.0 wt %, ≥ about 20.0 wt %, ≥ about 30.0 wt %, ≥ about 40.0 wt %, ≥ about 50.0 wt %, ≥ about 60.0 wt %, ≥ about 70.0 wt %, ≥ about 80.0 wt %, or ≥ about 90.0 wt %. Preferably, at least about 30.0 wt % or at least about 60.0 wt % of the $C_5$ hydrocarbons (e.g., acyclic $C_5$ hydrocarbons) is converted to cyclopentadiene. Ranges expressly disclosed include combinations of any of the above-enumerated values; e.g., about 5.0% to about 90.0 wt %, about 10.0 wt % to about 80.0 wt %, about 20.0 wt % to about 70.0 wt %, about 20.0 wt % to about 60.0 wt %, etc. Preferably, about 20.0 wt % to about 90.0 wt % of the $C_5$ hydrocarbons (e.g., acyclic $C_5$ hydrocarbons) is converted to cyclopentadiene, more preferably about 30.0 wt % to about 85.0 wt %, more preferably about 40.0 wt % to about 80.0 wt %, more preferably about 45.0 wt % to about 75.0 wt %, and more preferably about 50.0 wt % to about 70.0 wt %.

In various aspects, a co-feed comprising hydrogen and/or light hydrocarbons, such as $C_1$-$C_8$ hydrocarbons, preferably $C_1$-$C_4$ hydrocarbons, such as $C_1$-$C_4$ alkenes and/or $C_1$-$C_4$ alkanes, are also fed into the at least one reaction zone (discussed herein). In one or more embodiments, the co-feed comprises at least about 50 wt %, or 60 wt %, or 75 wt %, or 90 wt % hydrogen, or in the range from about 50 wt % to about 100 wt % hydrogen. In one or more embodiments, the co-feed comprises at least about 50 wt %, or 60 wt %, or 75 wt %, or 90 wt % light hydrocarbons, or in the range from about 50 wt % to about 100 wt % light hydrocarbons. In a particular embodiment, the co-feed may comprise hydrogen, ethane, methane and/or a mixture of ethane and ethylene. Preferably, the feedstock and co-feed are substantially free of oxygen, e.g., less than about 1.0 wt %, less than about 0.1 wt %, less than about 0.01 wt %, less than about 0.001 wt %, less than about 0.0001 wt %, less than about 0.00001 wt %, etc. Additionally, the feedstock and the co-feed may be provided to the at least one reaction zone at different locations via different inlets. Additionally, the feedstock and the co-feed may be provided to the at least one reaction zone simultaneously or not, preferably simultaneously. It is contemplated herein that co-feed and the feedstock are provided to the at least one reaction zone in different horizontal and/or vertical planes. For example, the co-feed may be provided to the at least one reaction zone at a lower position in the at least one reaction zone with respect to where the feedstock is provided, i.e., the feedstock may be provided to the at least one reaction zone at a position above (or higher than) where the co-feed is provided. In such instances, the co-feed and the feedstock may be provided to the at least one reaction zone at different horizontal planes, preferably where the co-feed is provided at a horizontal plane at a lower position in the at least one reaction zone with respect to horizontal plane where the feedstock is provided, and optionally, the co-feed and the feedstock may be provided along the same or different vertical plane. Alternatively, the co-feed may be provided to the at least one reaction zone at a position above (or higher than) where the feedstock is provided in the at least one reaction zone. In such instances, the co-feed and the feedstock may be provided to the at least one reaction zone at different horizontal planes, preferably where the co-feed is provided at a horizontal plane above (or higher than) a horizontal plane where the feedstock is provided, and optionally, the co-feed and the feedstock may be provided along the same or different vertical plane. Additionally, it is contemplated herein that the feedstock and the co-feed may be provided to the at least one reaction zone at substantially the same locations via the same or different inlet. Hydrogen may be provided to the reactor via the feedstock, the co-feed, or a combination of both. Preferably, hydrogen is included in both the feedstock and the co-feed. The presence of hydrogen in the feed mixture at or near the inlet location, where the feed first comes into contact with the catalyst, can prevent or reduce the formation of coke on the catalyst particles. Additionally, the presence of hydrogen in the co-feed can prevent or reduce the formation of coke in co-feed pre-heating furnaces.

B. Reaction Zone

The feedstock is fed into a reactor system and contacted with a catalyst material in at least one reaction zone under reaction conditions to convert at least a portion of the acyclic hydrocarbons (e.g., acyclic $C_5$ hydrocarbons) to a first effluent comprising alkenes (e.g., propylene), cyclic hydrocarbons (e.g., cyclopentadiene) and/or aromatics (e.g., benzene). For example, The at least one reaction zone may be a circulating fluidized bed reactor or a captive fluidized bed reactor. The circulating fluidized bed reactor may be operated in a bubbling or turbulent fluidization regime; and a fast fluidization or transport regime, both as described in Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. Additionally, or alternatively, the at least one reaction zone is not a radial-flow reactor or a cross-flow reactor.

Additionally, or alternatively, the at least one reaction zone may comprise at least a first reaction zone, a second reaction zone, a third reaction zone, a fourth reaction zone, a fifth reaction zone, a sixth reaction zone, a seventh reaction zone, and/or an eighth reaction zone, etc. As understood herein, each reaction zone may be an individual reactor or a reactor may comprise one or more of the reaction zones. Preferably, the reactor system includes 1 to 20 reaction zones, more preferably 1 to 15 reaction zones, more preferably 2 to 10 reaction zones, more preferably 2 to 8 reaction zones. Where the at least one reaction zone includes a first and a second reaction zone, the reaction zones may be arranged in any suitable configuration, preferably in series. Each reaction zone independently may be a circulating fluidized bed or a captive fluidized bed, preferably each reaction zone is a captive fluidized bed. Additionally, or alternatively, the process described herein may further comprise moving a bulk of a partially converted feedstock from the first reaction zone to the second reaction zone and/or moving a bulk of a particulate material (e.g., catalyst material and/or inert material) from the second reaction zone to the first reaction zone. As used herein, "bulk" refers to at least a majority portion of the partially converted feedstock and the particulate material, e.g., portions of at least about 50.0 wt %, at least about 60.0 wt %, at least about 70.0 wt %, at least about 80.0 wt %, at least about 90.0 wt %, at least about 95.0 wt %, at least about 99.0 wt %, and 100.0 wt %.

Preferably, the at least one reaction zone may include at least one internal structure, preferably a plurality of internal structures (e.g., 2, 3, 4, 5, 6, 7, 8, 9, 10, 15, 20, 30, 40, 50, etc.) to influence a velocity vector of the particulate material and/or gas flow. Further, the internal structure(s) can ensure movement of particulate material while minimizing the degree of gas back-mixing. Particularly, the at least one reaction zone may include a plurality of internal structures. Examples of suitable internal structures include a plurality of baffles, sheds, trays, tubes, tube bundles, tube coils, rods, and/or distributors.

The at least one reaction zone is operated under reaction conditions sufficient to convert at least a portion of the acyclic hydrocarbons feedstock, preferably acyclic $C_5$ hydrocarbons, to a first effluent comprising alkene, cyclic hydrocarbons, and aromatics, preferably cyclopentadiene. Preferably, the feedstock (e.g., acyclic hydrocarbons) and/or co-feed may be fed to the reaction system at a weight hourly space velocity (WHSV, mass of acyclic hydrocarbons/mass of catalyst/hour) in the range of from about 1.0 to about 1000.0 $hr^{-1}$. The WHSV may be about 1.0 to about 900.0 $hr^{-1}$, about 1.0 to about 800.0 $hr^{-1}$, about 1.0 to about 700.0 $hr^{-1}$, about 1.0 to about 600.0 $hr^{-1}$, about 1.0 to about 500.0 $hr^{-1}$, about 1.0 to about 400.0 $hr^{-1}$, about 1.0 to about 300.0 $hr^{-1}$, about 1.0 to about 200.0 $hr^{-1}$, about 1.0 to about 100.0 $hr^{-1}$, about 1.0 to about 90.0 $hr^{-1}$, about 1.0 to about 80.0 $hr^{-1}$, about 1.0 to about 70.0 $hr^{-1}$, about 1.0 to about 60.0 $hr^{-1}$, about 1.0 to about 50.0 $hr^{-1}$, about 1.0 to about 40.0 $hr^{-1}$, about 1.0 to about 30.0 $hr^{-1}$, about 1.0 to about 20.0 $hr^{-1}$, about 1.0 to about 10.0 $hr^{-1}$, about 1.0 to about 5.0 $hr^{-1}$, about 2.0 to about 1000.0 $hr^{-1}$, about 2.0 to about 900.0 $hr^{-1}$, about 2.0 to about 800.0 $hr^{-1}$, about 2.0 to about 700.0 $hr^{-1}$, about 2.0 to about 600.0 $hr^{-1}$, about 2.0 to about 500.0 $hr^{-1}$, about 2.0 to about 400.0 $hr^{-1}$, about 2.0 to about 300.0 $hr^{-1}$, about 2.0 to about 200.0 $hr^{-1}$, about 2.0 to about 100.0 $hr^{-1}$, about 2.0 to about 90.0 $hr^{-1}$, about 2.0 to about 80.0 $hr^{-1}$, about 2.0 to about 70.0 $hr^{-1}$, about 2.0 to about 60.0 $hr^{-1}$, about 2.0 to about 50.0 $hr^{-1}$, about 2.0 to about 40.0 $hr^{-1}$, about 2.0 to about 30.0 $hr^{-1}$, about 2.0 to about 20.0 $hr^{-1}$, about 2.0 to about 10.0 $hr^{-1}$, and about 2.0 to about 5.0 $hr^{-1}$. Preferably, the WHSV is about 1.0 to about 100.0 $hr^{-1}$, more preferably about 1.0 to about 60.0 $hr^{-1}$, more preferably about 2.0 to about 40.0 $hr^{-1}$, more preferably about 2.0 to about 20.0 $hr^{-1}$.

As discussed above, on-purpose production of CPD, propylene, ethylene, and benzene is accomplished via endothermic reactions, which present various challenges, such as maintaining high temperatures required for the reactions including transferring a large amount of heat to a catalyst). Advantageously, by pre-heating the co-feed via any suitable means, for example a furnace, such as a fired-tube furnace, the heated co-feed may provide the endothermic heat of reaction for the conversion process within the at least one reaction zone. In various aspects, the co-feed may contact the catalyst present in the at least one reaction zone and heat the catalyst, for example, where the co-feed is provided to the at least one reaction zone at a position lower than where the feedstock is provided. Thus, as the feedstock is provided to the at least one reaction zone, the feedstock may contact the heated catalyst and at least a portion of the acyclic hydrocarbons may be converted to alkenes, cyclic hydrocarbons and/or aromatics. Direct mixing or contacting of the heated co-feed and the acyclic feedstock, if both were to be fed using the same inlet of the reactor zone, would result in excessive thermal cracking of acyclic hydrocarbon(s) and formation of non-selective (C1-C4) light gases.

In particular, the co-feed provided to the at least one reaction may provide ≥ about 10%, ≥ about 20%, ≥ about 25%, ≥ about 30%, ≥ about 35%, ≥ about 40%≥ about 45%, ≥ about 50%, ≥ about 55%, ≥ about 60%, ≥ about 65%, ≥ about 70%, ≥ about 75%, ≥ about 80%, ≥ about 85%, ≥ about 90%, ≥ about 95%, or 100% of the required heat for converting at least a portion of the acyclic hydrocarbons to the first effluent comprising alkenes, cyclic hydrocarbons and/or aromatics, particularly converting acyclic $C_5$ hydrocarbons to cyclopentadiene. In particular, the co-feed may provide ≥25% of the required heat for converting at least a portion of the acyclic $C_5$ hydrocarbons to the first effluent comprising cyclopentadiene. Ranges expressly disclosed include combinations of any of the above-enumerated values; e.g., about 20% to about 100%, about 40% to about 95%, about 50% to about 90%, etc. Preferably, the co-feed may provide about 20% to about 100% of the required heat, more preferably 40% to about 100% of the required heat, or more preferably 50% to about 100% of the required heat.

In various aspects, following heating, the co-feed may enter the at least one reaction zone at a temperature of ≥ about 450° C., ≥ about 500° C., ≥ about 550° C., ≥ about 600° C., ≥ about 650° C., ≥ about 700° C., ≥ about 750° C., ≥ about 800° C., ≥ about 850° C., ≥ about 900° C., ≥ about 950° C., ≥ about 1000° C., ≥ about 1050° C., ≥ about 1100° C., ≥ about 1150° C., ≥ about 1200° C., ≥ about 1250° C., ≥ or about 1300° C. Preferably, the co-feed may enter the at least one reaction zone at a temperature of > about 600° C., more preferably > about 750° C., or more preferably > about 900° C. Ranges of temperatures expressly disclosed include combinations of any of the above-enumerated values, e.g., about 450° C. to about 1500° C., about 550° C. to about 1400° C., about 600° C. to about 1250° C., about 700° C. to about 1150° C., etc. Preferably, the temperature of the co-feed entering the reaction system is about 550° C. to about 1150° C. more preferably about 600° C. to about 1100° C., more preferably about 650° C. to about 1050° C., and more preferably about 700° C. to about 1000° C.

Thus, the feedstock may be heated to a lower temperature than the co-feed to avoid cracking in the feed and coking of the catalyst. Thus, the temperature of the feedstock (e.g., acyclic hydrocarbons) entering the reactor system at a feedstock inlet may be ≤ about 750° C., ≤ about 725° C., ≤ about 700° C., ≤ about 675° C., ≤ about 650° C., ≤ about 625° C., ≤ about 600° C., ≤ about 575° C., ≤ about 550° C., ≤ about 525° C., ≤ about 500° C., ≤ about 475° C., ≤ about 450° C., ≤ about 425° C., ≤ about 400° C., ≤ about 375° C., ≤ about 350° C., ≤ about 325° C., ≤ or about 300° C. Preferably, the temperature of the feedstock (e.g., acyclic hydrocarbons) entering the reactor system is ≤ about 700° C., more preferably ≤ about 650° C., or more preferably ≤ about 625° C. Ranges of temperatures expressly disclosed include combinations of any of the above-enumerated values, e.g., about 300° C. to about 750° C., about 350° C. to about 700° C., about 450° C. to about 650° C., about 475° C. to about 600° C., etc. Preferably, the temperature of the feedstock (e.g., acyclic hydrocarbons) entering the reaction system is about 300° C. to about 750° C., more preferably about 300° C. to about 700° C., more preferably about 400° C. to about 700° C., and more preferably about 575° C. to about 675° C. Providing the feedstock (e.g., acyclic $C_5$ hydrocarbons) at the above-described temperatures may advantageously minimize undesirable cracking of the $C_5$ hydrocarbons (e.g., acyclic $C_5$ hydrocarbons) before they can react in the presence of the catalyst material. The feedstock may be heated via any suitable means, for example a furnace, such as a fired-tube furnace and/or heat exchanger, prior to entering the at least one reaction zone.

Additionally, it may be preferable that an isothermal or substantially isothermal temperature profile be maintained in the at least one reaction zone. A substantially isothermal temperature profile has the advantages of maximizing the effective utilization of the catalyst and minimizing the production of undesirable C4-byproducts. As used herein, "isothermal temperature profile" means that the temperature at each point within the reaction zone between the reactor inlet and reactor outlet as measured along the tube centerline of the reactor is kept essentially constant, e.g., at the same temperature or within the same narrow temperature range wherein the difference between an upper temperature and a lower temperature is no more than about 40° C.; more preferably no more than about 20° C. Preferably, the isothermal temperature profile is one where the temperature along the length of the reaction zone(s) within the reactor does not vary by more than about 40° C. as compared to the average temperature within the reactor, alternately not more than about 20° C., alternately not more than about 10° C., alternately not more than about 5° C. Alternately, the isothermal temperature profile is one where the temperature along the length of the reaction zone(s) within the reactor is within about 20% of the average temperature within the reactor, alternately within about 10%, alternately within about 5%, alternately within about 1% of the average temperature within the reactor.

Additionally, the temperature of a first effluent exiting the at least one reaction zone at an effluent outlet may be ≥ about 400° C., ≥ about 425° C., ≥ about 450° C., ≥ about 475° C., ≥ about 500° C., ≥ about 525° C., ≥ about 550° C., ≥ about 575° C., ≥ about 600° C., ≥ about 625° C., ≥ about 650° C., ≥ about 675° C., or ≥ about 700° C. Preferably, the temperature of a first effluent exiting the at least one reaction zone is ≥ about 550° C., more preferably ≥ about 575° C., more preferably ≥ about 600° C. Ranges of temperatures expressly disclosed include combinations of any of the above-enumerated values, e.g., about 400° C. to about 700° C., about 475° C. to about 675° C., about 525° C. to about 650° C., about 550° C. to about 600° C., etc. Preferably, the temperature of a first effluent exiting the at least one reaction zone is about 475° C. to about 700° C., more preferably about 500° C. to about 650° C., more preferably about 550° C. to about 625° C.

Additionally, or alternatively, reaction conditions in the at least one reaction zone may include a temperature of ≥ about 300° C., ≥ about 325° C., ≥ about 350° C., ≥ about 375° C., ≥ about 400° C., ≥ about 425° C., ≥ about 450° C., ≥ about 475° C., ≥ about 500° C., ≥ about 525° C., ≥ about 550° C., ≥ about 575° C., ≥ about 600° C.≥ about 625° C., ≥ about 650° C., > about 675° C., or > about 700° C. Ranges of temperatures expressly disclosed include combinations of any of the above-enumerated values, e.g., about 300° C. to about 700° C., about 350° C. to about 675° C., and about 400° C. to about 700° C., etc. Preferably, the temperature may be about 350° C. to about 700° C., more preferably about 500° C. to about 700° C., or more preferably about 500° C. to about 650° C. Optionally, the at least one reaction zone may include one or more means for heating the at least one reaction zone in order to maintain a temperature therein. Examples of suitable heating means known in the art include, but are not limited to a fired tube, heat transfer tubes, a heated coil with a high temperature heat transfer fluid, an electrical heater, and/or a microwave emitter. As used herein, "coil" refers to a structure placed within a vessel through which a heat transfer fluid flows to transfer heat to the vessel contents. A coil may have any suitable cross-sectional shape and may be straight, include u-bends, include loops, etc.

Additionally, or alternatively, reaction conditions at the effluent outlet of the at least one reaction zone may include a pressure of ≥ about 1.0 psia, ≥ about 2.0 psia, ≥ about 3.0 psia, ≥ about 4.0 psia, ≥ about 5.0 psia, ≥ about 10.0 psia, ≥ about 15.0 psia, ≥ about 20.0 psia, ≥ about 25.0 psia, ≥ about 30.0 psia, ≥ about 35.0 psia, ≥ about 40.0 psia, ≥ about 45.0 psia, ≥ about 50.0 psia, ≥ about 55.0 psia, ≥ about 60.0 psia, ≥ about 65.0 psia, ≥ about 70.0 psia, ≥ about 75.0 psia, ≥ about 80.0 psia, ≥ about 85.0 psia, ≥ about 90.0 psia, ≥ about 95.0 psia, ≥ about 100.0 psia, ≥ about 125.0 psia, ≥ about 150.0 psia, ≥ about 175.0 psia or about 200 psia. Ranges and combinations of temperatures and pressures expressly disclosed include combinations of any of the above-enumerated values, e.g., about 1.0 psia to about 200.0 psia, about 2.0 psia to about 175.0 psia, about 5.0 psia to about 95.0 psia, etc. Preferably, the pressure may be about 3.0 psia to about 100.0 psia, more preferably about 3.0 psia to about 50.0 psia, more preferably about 3.0 psia to about 30.0 psia. In particular, the reaction conditions may comprise a temperature of about 500° C. to about 700° C. and a pressure of about 3.0 psia to about 100 psia.

Additionally, or alternatively, a delta pressure (or pressure drop) across the at least one reaction zone (pressure at feedstock inlet minus pressure at effluent outlet) may be ≥ about 0.5 psia, ≥ about 1.0 psia, ≥ about 2.0 psia, ≥ about 3.0 psia, ≥ about 4.0 psia, ≥ about 5.0 psia, ≥ about 10.0 psia, ≥ about 14.0 psia, ≥ about 15.0, psia, ≥ about 20.0 psia, ≥ about 24.0 psia, ≥ about 25.0 psia, ≥ about 30.0 psia, ≥ about 35.0 psia, ≥ about 40.0 psia, ≥ about 45.0 psia, ≥ about 50.0 psia, ≥ about 55.0 psia, ≥ about 60.0 psia, ≥ about 65.0 psia, ≥ about 70.0 psia, ≥ about 75.0 psia, ≥ about 80.0 psia, ≥ about 85.0 psia, ≥ about 90.0 psia, ≥ about 95.0 psia, ≥ about 100.0 psia, ≥ about 125.0 psia, or ≥ about 150.0 psia. As understood herein, "at a feedstock inlet," "at an inlet," "at an effluent outlet," and "at an outlet" includes the space in and substantially around the inlet and/or outlet. Additionally, or alternatively, a delta pressure (or pressure drop) across the at least one reaction zone (pressure at feedstock inlet minus pressure at effluent outlet) may be ≤ about 2.0 psia, ≤ about 3.0 psia, ≤ about 4.0 psia, ≤ about 5.0 psia, ≤ about 10.0 psia, ≤ about 14.0 psia, ≤ about 15.0 psia, ≤ about 20.0 psia, ≤ about 24.0 psia, ≤ about 25.0 psia, ≤ about 30.0 psia, ≤ about 35.0 psia, ≤ about 40.0 psia, ≤ about 45.0 psia, ≤ about 50.0 psia, ≤ about 55.0 psia, ≤ about 60.0 psia, ≤ about 65.0 psia, ≤ about 70.0 psia, ≤ about 75.0 psia, ≤ about 80.0 psia, ≤ about 85.0 psia, ≤ about 90.0 psia, ≤ about 95.0 psia, ≤ about 100.0 psia, ≤ about 125.0 psia, ≤ about 150.0 psia, ≤ about 175.0 psia, or ≤ about 200.0 psia. Ranges of delta pressures expressly disclosed include combinations of any of the above-enumerated values, e.g., about 10 psia to about 70.0 psia, about 20.0 psia to about 60.0 psia, about 30.0 psia to about 50.0 psia, etc. In particular, the pressure substantially at an inlet of a feedstock (e.g., acyclic $C_5$ hydrocarbons) may be about 10.0 psia to about 70.0 psia, preferably about 10.0 psia to about 60.0 psia, more preferably about 10.0 psia to about 40.0 psia. Additionally, the pressure substantially at an outlet of at least a first effluent may be about 1.0 psia to about 60.0 psia, preferably about 5 psia to about 40.0 psia, more preferably about 10.0 psia to about 30.0 psia.

C. Catalyst Material and Inert Material

The at least one reaction zone comprises particulate material including a catalyst material. The catalyst material, also referred to as a "catalyst composition," is present in the reaction system for promoting conversion of at least a portion of the acyclic hydrocarbons to alkenes, cyclic hydrocarbons and/or aromatics, in particular conversion of acyclic $C_5$ hydrocarbons to cyclopentadiene.

Catalyst compositions useful herein include microporous crystalline metallosilicates, such as crystalline aluminosilicates, crystalline ferrosilicates, or other metal-containing crystalline silicates (such as those where the metal or metal-containing compound is dispersed within the crystalline silicate structure and may or may not be a part of the crystalline framework). Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein, include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM-22 family materials) where one or more metals from groups 8, 11, and 13 of the Periodic Table of the Elements (preferably one or more of Fe, Cu, Ag, Au, B, Al, Ga, and/or In) are incorporated in the crystal structure during synthesis or impregnated post crystallization. It is recognized that a metallosilicate may have one of more metals present and, for example, a material may be referred to as a ferrosilicate, but it will most likely still contain small amounts of aluminum.

The microporous crystalline metallosilicates preferably have a constraint index of less than 12, alternately from 1 to 12, alternately from 3 to 12. Aluminosilicates useful herein have a constraint index of less than 12, such as 1 to 12, alternately 3 to 12, and include, but are not limited to Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family materials, and mixtures of two or more thereof. In a preferred embodiment, the crystalline aluminosilicate has a constraint index of about 3 to about 12 and is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829. ZSM-57 is described in U.S. Pat. No. 4,873,067. ZSM-58 is described in U.S. Pat. No. 4,698,217.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

In one or more embodiments, the crystalline metallosilicate has an Si/M molar ratio (where M is a group 8, 11, or 13 metal) greater than about 3, or greater than about 25, or greater than about 50, or greater than about 100, or greater than 400, or in the range from about 100 to about 2,000, or from about 100 to about 1,500, or from about 50 to 2,000, or from about 50 to 1,200.

In one or more embodiments, the crystalline aluminosilicate has an $SiO_2/Al_2O_3$ molar ratio greater than about 3, or greater than about 25, or greater than about 50, or greater than about 100, or greater than about 400, or greater than about 1,000, or in the range from about 100 to about 400, or from about 100 to about 500, or from about 25 to about 2,000, or from about 50 to about 1,500, or from about 100 to about 1,200, or from about 50 to about 1,000.

Typically, the microporous crystalline metallosilicate (such as an aluminosilicate) is combined with a Group 10 metal or metal compound and, optionally, one, two, three, or more additional metals selected from Groups 8, 9, 11, and 13 of the Periodic Table of the Elements and the rare earth metals, such as Ga, In, Zn, Cu, Re, Mo, W, La, Fe, Ag, Rh, Pr, La, and/or oxides, sulfides, nitrides, and/or carbides of these metals. Alternatively, or additionally, the Group 10 metal is present in combination with a Group I alkali metal and/or a Group 2 alkaline earth metal.

In one or more embodiments, the Group 10 metal includes, or is selected from the group consisting of, Ni, Pd, and Pt, preferably Pt. The Group 10 metal content of said catalyst composition is at least 0.005 wt %, based on the weight of the catalyst composition. In one or more embodiments, the Group 10 content is in the range from about 0.005 wt % to about 10 wt %, or from about 0.005 wt % up to about 1.5 wt %, based on the weight of the catalyst composition.

The Group 1 alkali metal is generally present as an oxide and the metal is selected from the group consisting of lithium, sodium, potassium, rubidium, cesium, and mixtures of two or more thereof. The Group 2 alkaline earth metal is generally present as an oxide and the metal is selected from the group consisting of beryllium, magnesium, calcium, strontium, barium, and mixtures of two or more thereof.

In one or more embodiments, the Group 11 metal includes, or is selected from the group consisting of, silver, gold, copper, preferably silver or copper. The Group 11 metal content of said catalyst composition is at least 0.005 wt %, based on the weight of the catalyst composition. In one or more embodiments, the Group 11 content is in the range from about 0.005 wt % to about 10 wt %, or from about 0.005 wt % up to about 1.5 wt %, based on the weight of the catalyst composition. In one or more embodiments, the molar ratio of said Group 11 metal to Group 10 metal is at least about 0.1, or from at least about 0.1 up to about 10, preferably at least about 0.5, more preferably at least about 1. In one or more embodiments, the Group 11 metal is present as an oxide.

A preferred Group 9 metal is Rh, which may form an alloy with the Group 10 metal. Preferably, the molar ratio of Rh to Group 10 metal is in the range from about 0.1 to about 5.

Typically, the rare earth metal is selected from the group consisting of yttrium, lanthanum, cerium, praseodymium, and mixtures or combinations thereof. Preferably, the molar ratio of rare earth metal to Group 10 metal is in the range from about 1 to about 10. The rare earth metal may be added to the catalyst composition during or after synthesis of the microporous crystalline molecular sieve as any suitable rare earth metal compound.

In one or more embodiments of aluminosilicates, the molar ratio of said Group 1 alkali metal to Al is at least about 0.5, or from at least about 0.5 up to about 3, preferably at least about 1, more preferably at least about 2.

In one or more embodiments of aluminosilicates, the molar ratio of said Group 2 alkaline earth metal to Al is at least about 0.5, or from at least about 0.5 up to about 3, preferably at least about 1, more preferably at least about 2.

In one or more embodiments, the catalyst composition has an Alpha Value (as measured prior to the addition of the Group 10 metal, preferably platinum) of less than 25, alternately less than 15, alternately from 1 to 25, alternately from 1.1 to 15. Alpha Value is determined as described in U.S. Pat. No. 3,354,078; The Journal of Catalysis, v. 4, p. 527 (1965); v. 6, p. 278 (1966); and v. 61, p. 395 (1980) using a constant temperature of 538° C. and a variable flow rate, as described in detail in The Journal of Catalysis, v. 61, p. 395, (1980).

In one or more embodiments, the use of any one of the catalyst compositions of this invention provides a conversion of at least about 70%, or at least about 75%, or at least about 80%, or in the range from about 60% to about 80%, of said acyclic $C_5$ feedstock under acyclic $C_5$ conversion conditions. This includes an n-pentane containing feedstock with equimolar $H_2$, a temperature in the range of about 550° C. to about 600° C., an n-pentane partial pressure between 3 and 10 psia, and an n-pentane weight hourly space velocity of 10 to 20 $hr^{-1}$.

In one or more embodiments, the use of any one of the catalyst compositions of this invention provides a carbon selectivity to cyclic $C_5$ compounds of at least about 30%, or at least about 40%, or at least about 50%, or in the range from about 30% to about 80%, under acyclic $C_5$ conversion conditions. This includes an n-pentane feedstock with equimolar $H_2$, a temperature in the range of about 550° C. to about 600° C., an n-pentane partial pressure between 3 and 10 psia, and an n-pentane weight hourly space velocity between 10 and 20 $hr^{-1}$.

In one or more embodiments, the use of any one of the catalyst compositions of this invention provides a carbon selectivity to cyclopentadiene of at least about 30%, or at least about 40%, or at least about 50%, or in the range from about 30% to about 80%, under acyclic $C_5$ conversion conditions. This includes an n-pentane feedstock with equimolar $H_2$, a temperature in the range of about 550° C. to about 600° C., an n-pentane partial pressure between 3 and 10 psia, and an n-pentane weight hourly space velocity between 10 and 20 $hr^{-1}$.

The catalyst compositions of this invention can be combined with a matrix or binder material to render them attrition resistant and more resistant to the severity of the conditions to which they will be exposed during use in hydrocarbon conversion applications. The combined compositions can contain 1 to 99 wt % of the materials of the invention based on the combined weight of the matrix (binder) and material of the invention. The relative proportions of microcrystalline material and matrix may vary widely, with the crystal content ranging from about 1 to about 90 wt % and, more usually, particularly when the composite is prepared in the form of beads, extrudates, pills, oil drop formed particles, spray dried particles, etc., in the range of about 2 to about 80 wt % of the composite. Preferred binder materials comprise one or more of silica, titania, zirconia, metal silicates of Group 1 or Group 13 of the Periodic Table, carbides, nitrides, aluminum phosphate, aluminum molybdate, aluminate, surface passivated alumina, and mixtures thereof. Preferably, suitable binder materials have a lower affinity for Group 10 metal particles, e.g. Pt, in comparison with the crystalline metallosilicate, e.g. aluminosilicate.

Useful catalyst compositions comprise a crystalline aluminosilicate or ferrosilicate, which is optionally combined with one, two, or more additional metals or metal compounds. Preferred combinations include:
1) a crystalline aluminosilicate (such as ZSM-5 or Zeolite L) combined with a Group 10 metal (such as Pt), a Group 1 alkali metal (such as sodium or potassium) and/or a Group 2 alkaline earth metal;
2) a crystalline aluminosilicate (such as ZSM-5 or Zeolite L) combined with a Group 10 metal (such as Pt), and a Group 1 alkali metal (such as sodium or potassium);
3) a crystalline aluminosilicate (such as a ferrosilicate or an iron treated ZSM-5) combined with a Group 10 metal (such as Pt) and a Group 1 alkali metal (such as sodium or potassium);
4) a crystalline aluminosilicate (Zeolite L) combined with a Group 10 metal (such as Pt) and a Group 1 alkali metal (such as potassium); and
5) a crystalline aluminosilicate (such as ZSM-5) combined with a Group 10 metal (such as Pt), a Group 1 alkali metal (such as sodium), and a Group 11 metal (such as silver or copper).

Another useful catalyst composition is a Group 10 metal (such as Ni, Pd, and Pt, preferably Pt) supported on silica (e.g., silicon dioxide) modified by a Group 1 alkali metal silicate (such as Li, Na, K, Rb, and/or $C_5$ silicates) and/or a Group 2 alkaline earth metal silicate (such as Mg, Ca, Sr, and/or Ba silicates), preferably potassium silicate, sodium silicate, calcium silicate, and/or magnesium silicate, preferably potassium silicate and/or sodium silicate. The Group 10 metal content of the catalyst composition is at least 0.005 wt %, based on the weight of the catalyst composition, preferably, in the range from about 0.005 wt % to about 10 wt %, or from about 0.005 wt % up to about 1.5 wt %, based on the weight of the catalyst composition. The silica ($SiO_2$) may be any silica typically used as catalyst support such as those marketed under the tradenames of DAVISIL 646 (Sigma Aldrich), DAVISON 952, DAVISON 948 or DAVISON 955 (Davison Chemical Division of W.R. Grace and Company).

Catalyst composition shape and design are preferably configured to minimize pressure drop, increase heat transfer, and minimize mass transport phenomena. Suitable catalyst shape and design are described in WO 2014/053553, which is incorporated by reference in its entirety. The catalyst composition may be an extrudate with a diameter of 2 mm to 20 mm. Optionally, the catalyst composition cross section may be shaped with one or more lobes and/or concave sections. Additionally, the catalyst composition lobes and/or concave sections may be spiraled. The catalyst composition may be an extrudate with a diameter of 2 mm to 20 mm; and the catalyst composition cross section may be shaped with one or more lobes and/or concave sections; and the catalyst composition lobes and/or concave sections may be spiraled. Also, the formulated catalyst composition may be made into a particle, such as, for example, a spray dried particle, an oil drop particle, a mulled particle, or a spherical particle. The formulated catalyst composition may be made into a slurry. Such slurry materials typically contain the microporous crystalline metallosilicate, such as zeolite, and a filler such as a silicate. For fluid bed reactors, spherical particle shapes are particularly useful.

For more information on useful catalyst compositions, please see applications:
1) U.S. Ser. No. 62/250,675, filed Nov. 4, 2015;
2) U.S. Ser. No. 62/250,681, filed Nov. 4, 2015;
3) U.S. Ser. No. 62/250,688, filed Nov. 4, 2015;
4) U.S. Ser. No. 62/250,695, filed Nov. 4, 2015; and
5) U.S. Ser. No. 62/250,689, filed Nov. 4, 2015; which are incorporated herein by reference.

Preferably, the catalyst material comprises platinum on ZSM-5, platinum on zeolite L, and/or platinum on silica.

In addition to the catalyst material, inert material may also be present in the at least one reaction zone. As referred to herein, the inert material is understood to include materials which promote a negligible amount promote a negligible amount (e.g., ≤ about 3%, ≤ about 2%, ≤ about 1%, etc.) of conversion of the feedstock, intermediate products, or final products under the reaction conditions described herein. In various aspects, the catalyst material and/or the inert material may have an average diameter of ≥ about 10 μm≥ about 25 μm, ≥ about 50 μm, ≥ about 100 μm, ≥ about 200 μm, ≥ about 300 μm, ≥ about 400 μm, ≥ about 500 μm, ≥ about 600 μm, ≥ about 700 μm, ≥ about 800 μm, ≥ about 900 μm, ≥ about 1000 μm. Additionally, or alternatively, the catalyst material and/or the inert material may have an average diameter of ≤ about 50 μm, ≤ about 100 μm, ≤ about 200 μm, ≤ about 300 μm, ≤ about 400 μm, ≤ about 500≤ about 600 μm, ≤ about 700 μm, ≤ about 800 μm, ≤ about 900 μm, ≤ about 1000 μm. Ranges expressly disclosed include combinations of any of the above-enumerated values, e.g., about 10 μm to about 1,000 μm, about 50 μm to about 500 μm, about 100 μm to about 750 μm, about 200 μm to about 500 μm, etc. Preferably, in a circulating fluidized bed or a captive fluidized bed reactor, the catalyst material and/or the inert material may have an average diameter of about 20 μm to about 300 μm, more preferably about 20 μm to about 100 μm, more preferably about 40 μm to about 90 μm, more preferably about 50 μm to about 80 μm.

The catalyst material and the inert material may be combined as portions of the same particles and/or may be separate particles. Preferably the catalyst material and the inert material are separate particles. Additionally, the catalyst material and/or inert material may be essentially spherical (i.e., < about 20%, < about 30%, < about 40%, or < about 50% aberration in diameter). Examples of suitable inert materials include, but are not limited to metal carbides (e.g., silicon carbide, tungsten carbide, etc.), metal oxides (e.g., silica, zirconia, titania, alumina, etc.), clays, metal phosphates (e.g., aluminum phosphates, nickel phosphates, zirconium phosphates, etc.), and combinations thereof. In particular, the inert material may comprise silicon carbide, silica, and a combination thereof.

D. Effluent

An effluent (e.g., first effluent, second effluent) exiting the at least one reaction zone may comprise a variety of hydrocarbon compositions produced from the reaction of the acyclic hydrocarbons (e.g., acyclic $C_5$ hydrocarbons) in the at least one reaction zone. The hydrocarbon compositions typically have mixtures of hydrocarbon compounds, such as alkenes, cyclic hydrocarbons, and aromatics, having from 1 to 30 carbon atoms ($C_1$-$C_{30}$ hydrocarbons), from 1 to 24 carbon atoms ($C_1$-$C_{24}$ hydrocarbons), from 1 to 18 carbon atoms ($C_1$-$C_{18}$ hydrocarbons), from 1 to 10 carbon atoms ($C_1$-$C_{10}$ hydrocarbons), from 1 to 8 carbon atoms ($C_1$-$C_8$ hydrocarbons), and from 1 to 6 carbon atoms ($C_1$-$C_6$ hydrocarbons). Particularly, the first effluent comprises cyclopentadiene. The cyclopentadiene may be present in a hydrocarbon portion of an effluent (e.g., first effluent, second effluent) in an amount of ≥ about 20.0 wt %, ≥ about 25.0 wt %, ≥ about 30.0 wt %, ≥ about 35.0 wt %, ≥ about 40.0 wt %, ≥ about 45.0 wt %, ≥ about 50.0 wt %, ≥ about 55.0 wt %, ≥ about 60.0 wt %, ≥ about 65.0 wt %, ≥ about 70.0 wt %, ≥ about 75.0 wt %, or ≥ about 80.0 wt %. Additionally, or alternatively, the cyclopentadiene may be present in a hydrocarbon portion of an effluent (e.g., first effluent, second effluent) in an amount of ≤ about 20.0 wt %, ≤ about 25.0 wt %, ≤ about 30.0 wt %, ≤ about 35.0 wt %, ≤ about 40.0 wt %, ≤ about 45.0 wt %, ≤ about 50.0 wt %, ≤ about 55.0 wt %, ≤ about 60.0 wt %, ≤ about 65.0 wt %, ≤ about 70.0 wt %, ≤ about 75.0 wt %, ≤ about 80.0 wt %, or ≤ about 85.0 wt %. Ranges expressly disclosed include combinations of any of the above-enumerated values, e.g., about 20.0 wt % to about 85.0 wt %, about 30.0 wt % to about 75.0 wt %, about 40.0 wt % to about 85.0 wt %, about 50.0 wt % to about 85.0 wt %, etc. Preferably, the cyclopentadiene may be present in a hydrocarbon portion of an effluent (e.g., first effluent, second effluent) in an amount of about 10.0 wt % to about 85.0 wt %, more preferably about 25.0 wt % to about 80.0 wt %, more preferably about 40.0 wt % to about 75.0 wt %.

In other aspects, an effluent (e.g., first effluent, second effluent) may comprise one or more other $C_5$ hydrocarbons in addition to cyclopentadiene. Examples of other $C_5$ hydrocarbons include, but are not limited to cyclopentane and cyclopentene. The one or more other $C_5$ hydrocarbons may be present in a hydrocarbon portion of an effluent (e.g., first effluent, second effluent) in an amount ≥ about 10.0 wt %, ≥ about 15.0 wt %, ≥ about 20.0 wt %, ≥ about 25.0 wt %, ≥ about 30.0 wt %, ≥ about 35.0 wt %, ≥ about 40.0 wt %, ≥ about 45.0 wt %, ≥ about 50.0 wt %, ≥ about 55.0 wt %, ≥ about 60.0 wt %, ≥ about 65.0 wt %, or ≥ about 70.0 wt %. Additionally, or alternatively, the one or more other $C_5$ hydrocarbons may be present in a hydrocarbon portion of an effluent (e.g., first effluent, second effluent) in an amount of ≤ about 15.0 wt %, ≤ about 20.0 wt %, ≤ about 25.0 wt %, ≤ about 30.0 wt %, ≤ about 35.0 wt %, ≤ about 40.0 wt %, ≤ about 45.0 wt %, ≤ about 50.0 wt %, ≤ about 55.0 wt %, ≤ about 60.0 wt %, ≤ about 65.0 wt %, or ≤ about 70.0 wt %. Ranges expressly disclosed include combinations of any of the above-enumerated values, e.g., about 10.0 wt % to about 70.0 wt %, about 10.0 wt % to about 55.0 wt %, about 15.0 wt % to about 60.0 wt %, about 25.0 wt % to about 65.0 wt %, etc. Preferably, the one or more other $C_5$ hydrocarbons may be present in a hydrocarbon portion of an effluent (e.g., first effluent, second effluent) in an amount of about 30.0 wt % to about 65.0 wt %, more preferably about 20.0 wt % to about 40.0 wt %, more preferably about 10.0 wt % to about 25.0 wt %.

In other aspects, an effluent (e.g., first effluent, second effluent) may also comprise one or more aromatics, e.g., having 6 to 30 carbon atoms, particularly 6 to 18 carbon atoms. The one or more aromatics may be present in a hydrocarbon portion of an effluent (e.g., first effluent, second effluent) in an amount of about ≥ about 1.0 wt %, ≥ about 5.0 wt %, ≥ about 10.0 wt %, ≥ about 15.0 wt %, ≥ about 20.0 wt %, ≥ about 25.0 wt %, ≥ about 30.0 wt %, ≥ about 35.0 wt %, ≥ about 40.0 wt %, ≥ about 45.0 wt %, ≥ about 50.0 wt %, ≥ about 55.0 wt %, ≥ about 60.0 wt %, or ≥ about 65.0 wt %. Additionally, or alternatively, the one or more aromatics may be present in a hydrocarbon portion of an effluent (e.g., first effluent, second effluent) in an amount of ≤ about 1.0 wt %, ≤ about 5.0 wt %, ≤ about 10.0 wt %, ≤ about 15.0 wt %, ≤ about 20.0 wt %, ≤ about 25.0 wt %, ≤ about 30.0 wt %, ≤ about 35.0 wt %, ≤ about 40.0 wt %, ≤ about 45.0 wt %, ≤ about 50.0 wt %, ≤ about 55.0 wt %, ≤ about 60.0 wt %, or ≤ about 65.0 wt %. Ranges expressly disclosed include combinations of any of the above-enumerated values, e.g., about 1.0 wt % to about 65.0 wt %, about 10.0 wt % to about 50.0 wt %, about 15.0 wt % to about 60.0 wt %, about 25.0 wt % to about 40.0 wt %, etc. Preferably, the one or more aromatics may be present in a hydrocarbon portion of an effluent (e.g., first effluent, second effluent) in an amount of about 1.0 wt % to about 15.0 wt %, more preferably about 1.0 wt % to about 10 wt %, more preferably about 1.0 wt % to about 5.0 wt %.

For information on possible dispositions of the effluents, please see applications:
1) U.S. Ser. No. 62/250,678, filed Nov. 4, 2015;
2) U.S. Ser. No. 62/250,692, filed Nov. 4, 2015;
3) U.S. Ser. No. 62/250,702, filed Nov. 4, 2015; and
4) U.S. Ser. No. 62/250,708, filed Nov. 4, 2015; which are incorporated herein by reference.

E. Stripping/Separation of the Effluent

In various aspects, catalyst material and/or inert material may become entrained with hydrocarbons (e.g., cyclopentadiene) in the effluent (e.g., first effluent, second effluent) as the effluent travels through and/or exits the at least one reaction zone. Thus, the process may further comprise separating catalyst material and/or inert material, which may be entrained with hydrocarbons (e.g., cyclopentadiene) in the effluent (e.g., first effluent, second effluent). This separating may comprise removal of the catalyst material and/or inert material from the hydrocarbons (e.g., cyclopentadiene) by any suitable means, such as, but not limited to cyclones, filter, electrostatic precipitators, heavy liquid contacting, and/or other gas solid separation equipment, which may be inside and/or outside the at least one reaction zone. The effluent substantially free of particulate material may then travel to a product recovery system. Additionally, the separated catalyst material and/or inert material may then be fed back into the at least one reaction zone at any desirable location. In a particular embodiment, a separated catalyst material stream may be introduced into the at least one reaction zone at a position above where feedstock and co-feed are provided to the at least one reaction.

Additionally, or alternatively, co-feed may also be separated from the effluent (e.g., first effluent, second effluent) via any suitable means or combinations thereof such as distillation, adsorption (pressure-swing or temperature-swing), membrane separation, liquid/solvent absorption, condensation, etc. and the separated co-feed may be recycled back to the at least one reaction zone. Preferably, the separated co-feed is heated as described above before being reintroduced into the at least one reaction zone.

Additionally, or alternatively, the separated material with reduced level of hydrocarbons may then travel to a rejuvenation zone, and/or regeneration zone, and the hydrocarbons stripped from the particulate material may be directed to the product recovery system or to the reactor system.

F. Rejuvenation

As the reaction occurs in the at least one reaction zone, coke material may form on the particulate material, particularly on the catalyst material, which may reduce the activity of the catalyst material. Additionally, or alternatively, the particulate material may cool as the reaction occurs. The catalyst material exiting the at least one reaction zone is referred to as "spent catalyst material." Thus, the effluent and the separate catalyst material can comprise spent catalyst material. This spent catalyst material may not necessarily be a homogenous mix of particles as individual particles may have had a distribution of total aging in the system, time since last regeneration and/or rejuvenation, and/or ratio of times spent in reaction zones relative to in the regeneration and/or rejuvenation zones.

Thus, at least a portion of the particulate material (e.g., spent catalyst material) may be transferred from the at least one reaction zone to a rejuvenation zone to produce rejuvenated catalyst material. The transferring of the particulate material (e.g., spent catalyst material) from the at least one reaction zone to a reheating zone may occur after the catalyst material has been stripped and/or separated from the hydrocarbons after exiting the at least one reaction zone. Additionally, or alternatively, catalyst (e.g., spent catalyst material) material may be transferred directly from the at least one reaction zone to a reheating zone. The reheating zone may include one more heating devices, such as but not limited to direct contacting, a heating coil, and/or a fired tube.

In various aspects, in the rejuvenation zone, the particulate material (e.g., spent catalyst material) may be contacted with a gaseous stream comprising hydrogen and substantially free of reactive oxygen-containing compounds to remove at least a portion of incrementally deposited coke material on the catalyst material thereby forming a rejuvenated catalyst material and a volatile hydrocarbon, such as, but not limited to methane. As used herein, the term "incrementally deposited" coke material refers to an amount of coke material that is deposited on the catalyst material during each pass of the catalyst material through the at least one reaction zone as opposed to a cumulative amount of coke material deposited on the catalyst material during multiple passes through the at least one reaction zone. "Substantially free" used in this context means the rejuvenation gas comprises less than about 1.0 wt %, based upon the weight of the gaseous stream, e.g., less than about 0.1 wt %, less than about 0.01 wt %, less than about 0.001 wt %, less than about 0.0001 wt %, less than about 0.00001 wt % oxygen-containing compounds. The gaseous stream may comprise ≥50 wt % $H_2$, such as ≥60 wt %, ≥70 wt %, preferably ≥90 wt % $H_2$. The gaseous stream may further comprise an inert substance (e.g., $N_2$), and/or methane. Contacting the spent catalyst material with the gaseous stream may occur at a temperature of about 500° C. to about 900° C., preferably about 575° C. to about 750° C. and/or at a pressure between about 5.0 psia to about 250 psia, preferably about 25 psia to about 250 psia.

In alternative aspects, in the rejuvenation zone, the particulate material (e.g., spent catalyst material) may be rejuvenated via a mild oxidation procedure comprising contacting the particulate material with an oxygen-containing gaseous stream under conditions effective to remove at least a portion of incrementally deposited coke material on the catalyst material thereby forming a rejuvenated catalyst material. Typically, these conditions include a temperature range of about 250° C. to about 500° C., and a total pressure of about 0.1 bar to about 100 bar, preferably at atmospheric pressure. Further, the oxygen-containing gaseous stream is typically supplied to the rejuvenation zone at a total WHSV in the range of about 1 to 10,000. Following the mild oxidation, purge gas is generally reintroduced to purge oxidants from the catalyst composition using a purge gas, for example, $N_2$. This purging step may be omitted if $CO_2$ is the oxidant as it will not produce a flammable mixture. Optionally, rejuvenation via mild oxidation further comprises one or more hydrogen treatment steps.

In any embodiment, the rejuvenated catalyst material may then be returned to the at least one reaction zone.

In any embodiment, rejuvenation is generally effective at removing at least 10 wt % (≥10 wt %) of incrementally deposited coke material. Between about 10 wt % to about 100 wt %, preferably between about 60 wt % to about 100 wt %, more preferably between about 90 wt % to about 100 wt % of incrementally deposited coke material is removed.

Rejuvenation advantageously may have a time duration of ≤90 mins, e.g., ≤60 mins, ≤30 mins, ≤10 mins, such as ≤1 min, or ≤10 seconds. Rejuvenation may be advantageously performed ≥10 minutes, e.g., ≥30 minutes, ≥2 hours, ≥5 hours, ≥24 hours, ≥2 days, ≥5 days, ≥20 days, after beginning the specified conversion process.

Rejuvenation effluent exiting the rejuvenation zone and comprising, unreacted hydrogen, coke particulate, and optionally light hydrocarbon, may be further processed. For example, in aspects where rejuvenation is achieved via contact with a hydrogen-rich gaseous stream, the rejuvenation effluent may be sent to a compression device and then sent to a separation apparatus wherein a light hydrocarbon enriched gas and light hydrocarbon depleted gas is produced. The light hydrocarbon gas may be carried away, e.g., for use as fuel gas. The light hydrocarbon depleted stream may be combined with make-up hydrogen and make up at least a portion of the gaseous stream provided to the rejuvenation zone. The separation apparatus may be a membrane system, adsorption system (e.g., pressure swing or temperature swing), or other known system for separation of hydrogen from light hydrocarbons. A particulate separation device, e.g., a cyclonic separation drum, may be provided wherein coke particulate is separated from the rejuvenation effluent.

G. Regeneration

The process may further comprise a regeneration step to recapture catalyst activity lost due to the accumulation of coke material and/or agglomeration of metal on the catalyst material during the reaction. This regeneration step may be carried out when there has not been sufficient removal of the coke material from the particulate material (e.g., spent catalyst material) in the rejuvenation zone.

Preferably, in the regeneration step, at least a portion of the spent catalyst material from the at least one reaction zone, from the separated catalyst material following stripping from the effluent, and/or from the rejuvenation zone may be transferred to a regeneration zone and regenerated by methods known in the art. For example, an oxidative regeneration may be used to remove at least a portion of coke material from the spent catalyst material. In various aspects, a regeneration gas comprising an oxidizing material such as oxygen, for example, air, may contact the spent catalyst material. The regeneration gas may oxidatively remove at least 10 wt % (≥10 wt %) of the total amount of coke material deposited on the catalyst composition at the start of regeneration. Typically, an oxychlorination step is performed following coke removal comprising contacting the catalyst composition with a gaseous stream comprising a chlorine source and an oxygen source under conditions effective for dispersing at least a portion of metal, e.g., Group 10 metal, particles on the surface of the catalyst and to produce a metal chlorohydrate, e.g., a Group 10 metal chlorohydrate. Additionally, a chlorine stripping step is typically performed following oxychlorination comprising contacting the catalyst composition with a gaseous stream comprising an oxygen source, and optionally a chlorine source, under conditions effective for increasing the O/Cl ratio of the metal chlorohydrate. Generally, a reduction step, and optionally a sulfidation step may also be performed in the regeneration step. Typically, regeneration is effective at removing between about 10 wt % to about 100 wt %, preferably between about 90 wt % to about 100 wt % of coke material is removed. Optionally, before or after contacting the spent catalyst material with the regeneration gas, the catalyst material may also be contacted with a purge gas, e.g., $N_2$. Regeneration, including purging before and after coke oxidation, requires less than 10 days, preferably less than about 3 days to complete.

Catalyst may be continuously withdrawn from and returned to the reaction zone and/or the rejuvenation zone or may be periodically withdrawn from and returned to the reaction zone and/or regeneration zone. For a periodic method, typically, the regeneration times between when withdrawals are made for coke burn, oxychlorination, chlorine stripping, purge, reduction, and optional sulfidation occurs are between about 24 hours (about 1 day) to about 240 hours (about 10 days), preferably between about 36 hours (about 1.5 days) to about 120 hours (about 5 days). Alternatively for continuous mode, the removal/addition of particulate material rate may vary between about 0.0 wt % to about 100 wt % (e.g., about 0.01 wt % to about 100 wt %) per day of the particulate material inventory, and preferably between about 0.25 wt % to about 30.0 wt % per day of the particulate material inventory where there is balanced addition/removal of particulate material. Regeneration of the catalyst material may occur as a continuous process or may be done batch wise in both cases intermediate vessels for inventory accumulation and/or inventory discharge may be required.

The removal and addition of the particulate material (e.g., spent catalyst material, fresh catalyst material, fresh inert material, rejuvenated catalyst material, regenerated catalyst material) may occur at the same or different location in the reactor system. The particulate material (e.g., fresh catalyst material, fresh inert material, rejuvenated catalyst material, regenerated catalyst material) may be added after or before the rejuvenation zone, while the removal of the particulate material (e.g., spent catalyst material) may be done before or after the particulate material (e.g., spent catalyst material) is passed through the rejuvenation zone. At least a portion of the regenerated catalyst material may be recycled to the at least one reaction zone or at least one rejuvenation zone. Preferably, the regenerated catalyst material and/or fresh particulate material are provided to the rejuvenation zone to minimize any loss in heat input and to remove any remaining species that may be carried by the regenerated catalyst material from the regeneration zone. Additionally, or alternatively, separators inside or outside of the regeneration zone may be used to separate the inert material from the catalyst material prior to regeneration so that just the catalyst material is regenerated. This separation may be carried out on the basis of size, magnetic, and/or density property differences between the inert material and the regenerated catalyst material using any suitable means.

For the above-described processes, standpipes, well known by those skilled in the art with the particle size and operating conditions described above, may be used to provide the means of transporting the particulate material between the at least one reaction zone, rejuvenation zone, and/or regeneration zone. Slide valves and lifting gas, known by those skilled in the art, may also be used to help circulate the particulate material and/or build the necessary pressure profile inside the regeneration zone. The lifting gas may be the same as the fluidizing gas used in the rejuvenation zone, e.g., a hydrogen stream that may contribute in minimizing the hydrogen usage in the reaction system, while also reducing the coke material formation.

III. Reaction Systems for Conversion of Acyclic Hydrocarbons

In another embodiment, a reaction system 1 for converting acyclic hydrocarbons (e.g., acyclic $C_5$ hydrocarbons) to alkenes, cyclic hydrocarbons (e.g., cyclopentadiene) and/or aromatics is provided, as shown in the FIGURE. The reaction system 1 may comprise a feedstock stream 2, a co-feed stream 3, at least one reactor 10, and an effluent stream 11. The feedstock stream 2 may comprise an acyclic hydrocarbon (e.g., acyclic $C_5$ hydrocarbons, such as pentane) stream 2a as described above, and optionally, a first hydrogen stream 2b. The co-feed stream 3 may comprise a light hydrocarbon (e.g., $C_1$-$C_4$ alkanes and/or $C_1$-$C_4$ alkene) stream 3a as described above and a second hydrogen stream 3b. In particular, the co-feed stream 3 may comprise hydrogen, ethane, methane and/or a mixture of ethane and ethylene. The reaction system 1 may further comprise a first furnace 4 for heating the feedstock stream 2 to produce a heated feedstock stream 5, which may be provided to the least one reactor 10 at feedstock temperatures as described herein (e.g., about 300° C. to about 700° C.). For example, a first fuel gas stream 6 may be provided to the first furnace 4 for heating the feedstock stream 2. Additionally, reaction system 1 may further comprise a second furnace 7 for heating the co-feed stream 3 to produce a heated co-feed stream 8, which may be provided to at least one reactor 10 at co-feed temperatures as described herein (e.g., about 600° C. to about 1100° C.) and which may heat catalyst material present in the at least one reactor 10. For example, a second fuel gas stream 9 may be provided to the second furnace 7 for heating the co-feed stream 3. The at least one reactor 10 may comprise a feedstock stream inlet (not shown) for providing the heated feedstock stream 5 to the reaction system, a co-feed stream inlet (not shown) for providing the heated co-feed stream 8, and an effluent stream outlet (not shown) for removal of the effluent stream 11. In a particular embodiment, the feedstock stream inlet (not shown) is a position in the at least one reactor 10 above the co-feed stream inlet (not shown).

The at least one reactor 10 may be a circulating fluidized bed reactor or a captive fluidized bed reactor, preferably a captive fluidized bed reactor. Additionally, or alternatively, the at least one reactor is not a radial-flow reactor or a cross-flow reactor.

Additionally, or alternatively, the reaction system 1 may comprise at least a first reactor, a second reactor, a third reactor, a fourth reactor, a fifth reactor, a sixth reactor, a seventh reactor, etc. As used herein, each "reactor" may be individual vessels or individual reaction zones within a single vessel. Preferably, the reaction system includes 1 to 20 reactors, more preferably 1 to 15 reactors, more preferably 2 to 10 reactors, more preferably 3 to 8 reactors. A circulating fluidized bed reactor may include multiple reaction zones (e.g., 3-8) within a single vessel or multiple vessels (e.g., 3-8). Where the reaction system includes more than one reactor, the reactors may be arranged in any suitable configuration, preferably in series, wherein a bulk of the feedstock moves from the first reactor to the second reactor and/or a bulk of the particulate material moves from the second reactor to the first reactor, and so on. Each reactor, independently, may be a circulating fluidized bed reactor or a captive fluidized bed reactor.

Preferably, the at least one reactor 10 may include at least one or more internal structures 8, as described above. Particularly, the at least one reactor 10 may include a plurality of internal structures (e.g., 2, 3, 4, 5, 6, 7, 8, 9, 10, 15, 20, 30, 40, 50, etc.), such as, baffles, sheds, trays, tubes, tube bundles, tube coils, rods, and/or distributors.

The at least one reactor 10 is operated under reaction conditions as described above to convert at least a portion of the acyclic hydrocarbons (e.g., acyclic $C_5$ hydrocarbons) to alkenes, cyclic hydrocarbons (e.g., cyclopentadiene), and/or aromatics. For example, the reaction conditions may comprise a temperature of about 500° C. to about 700° C. and/or a pressure of about 3.0 psia to about 100 psia. Preferably, at least about 30 wt % of the acyclic $C_5$ hydrocarbons is converted to cyclopentadiene. Optionally, the at least one reactor 10 may include one or more heating means (e.g., fired tube, heated coil, heat transfer tubes) (not shown) as described herein in order to maintain temperature therein.

Additionally, the reaction system 1 may further comprise a separator 12, such as a cyclone, (one is shown, but two or more operating in series may be present with one or more operating in parallel) in fluid connection with the at least one reactor 10. The separator 12 may be located externally (as shown) or internally (not shown) within the reactor. The separator 12, may separate the catalyst material, which may be entrained with hydrocarbons (e.g., cyclopentadiene) in the effluent stream 11 to produce a separated catalyst material stream 14 and a substantially catalyst-free effluent stream 13. The substantially catalyst-free effluent stream 13 may comprise a lower amount of catalyst material than the effluent stream 11, preferably the substantially catalyst-free effluent stream 13 comprises a negligible amount (e.g., ≤ about 5.0 wt %, ≤ about 2.0 wt %, ≤ about 1.0 wt %) of catalyst material or no catalyst material. The substantially catalyst-free effluent stream 13 may optionally travel to a product recovery system. Additionally, the separated catalyst material stream 14 may then be fed back into the at least one reactor 10 (the material may be returned at a position above where the heated feedstock stream 5 enters) via a separated catalyst material inlet (not shown) in the at least one reactor 10. The separator 12 may comprise an effluent stream inlet (not shown), a separated catalyst material stream outlet (not shown), and a substantially catalyst-free effluent stream outlet (not shown). Optionally, a third hydrogen stream 15 may be present in the reaction system 1, which may be fed to the first separator 12 and/or combined with the separated catalyst material stream 14.

Additionally, or alternatively, the reaction system 1 may further comprise a rejuvenating and/or regenerating apparatus 16 for restoring activity of the spent catalyst material, wherein the rejuvenating and/or regenerating apparatus 16 is in fluid connection with the at least one reactor 10. For example, a spent catalyst stream 17 comprising at least a portion of the separated catalyst material stream 14 may be provided to the rejuvenating and/or regenerating apparatus 16 to produce a rejuvenated and/or regenerated catalyst stream 18 which can be combined with the separated catalyst material stream 14 or alternatively, enter the reactor through a separate outlet (not shown).

Additionally, or alternatively, the reaction system 1 may further comprise a fresh catalyst material stream (not shown) in fluid connection with the at least one reactor 10.

IV. Industrial Applicability

A first hydrocarbon reactor effluent obtained during the acyclic $C_5$ conversion process containing cyclic, branched, and linear $C_5$ hydrocarbons and, optionally, containing any combination of hydrogen, $C_4$ and lighter byproducts, or $C_6$ and heavier byproducts is a valuable product in and of itself. Preferably, CPD and/or DCPD may be separated from the reactor effluent to obtain purified product streams which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

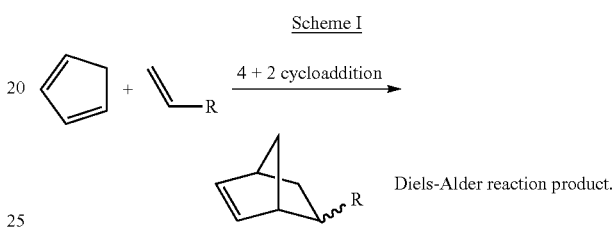

Scheme I where R is a heteroatom or substituted heteroatom, substituted or unsubstituted $C_1$-$C_{50}$ hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the mono-olefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins, and substituted versions of the foregoing. Preferred Diels-Alder reaction products include norbornene, ethylidene norbornene, substituted norbornenes (including oxygen-containing norbornenes), norbornadienes, and tetracyclododecene, as illustrated in the following structures:

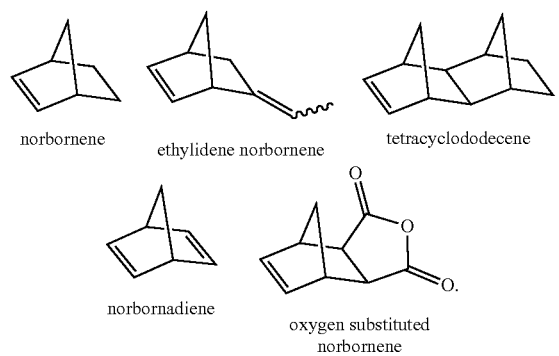

The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

Scheme II

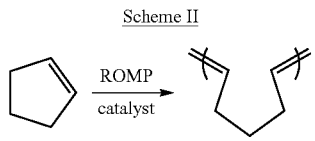

Separated cyclopentane is useful as a blowing agent and as a solvent. Linear and branched $C_5$ products are useful for conversion to higher olefins and alcohols. Cyclic and non-cyclic $C_5$ products, optionally after hydrogenation, are useful as octane enhancers and transportation fuel blend components.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

PROPHETIC EXAMPLES

The following examples are derived from modeling techniques and although the work was actually achieved, the inventors do not present these examples in the past tense to comply with M.P.E.P. § 608.01(p) if so required.

Example 1—Reactor Performance Modeling

Reactor modeling was performed using Invensys Systems Inc. PRO/II 9.3.4 for the purpose of estimating the performance at various commercially relevant operating conditions. Depending on specifics of the modeling, variation in results will occur but the models will still demonstrate the relative benefits of the present invention. Numerous modifications and variations are possible and it is to be understood that within the scope of the claims, the invention may be practiced otherwise than as specifically described herein.

Example 1A—Methane Diluent, 20 Psia Outlet Pressure, 10 Psia HC Partial Pressure A 20 psia outlet pressure, 575° C. outlet temperature, fluidized bed reactor is simulated with a feed comprising of n-pentane, which is pre-heated to 621° C. prior to feeding into the fluidized bed, and a co-feed comprising of methane and hydrogen, which is separately pre-heated to a temperature required to supply 100% of the heat of reaction. Under these conditions, the catalyst is assumed to have a lights selectivity (C4-products) of ~18%. The residence time within the catalyst bed is assumed to provide for CPD concentration to reach its thermodynamic concentration at the reactor outlet conditions. The hydrogen molar rate in reactor co-feed is set to deliver a molar ratio of hydrogen:n-pentane in feed of 1:1. The methane molar rate in reactor co-feed is set to deliver a methane partial pressure at reactor outlet of 10 psia (i.e., combined partial pressure of all other hydrocarbons including hydrogen of 10 psia). Based on the reactor yields, this corresponds to a molar ratio of methane:n-pentane in feed of about 4:1. To generate 1 lb-mole of CPD in the fluidized bed reactor effluent, it is determined from the simulation that 2.195 lb-moles of n-Pentane, 8.741 lb-moles of methane and a co-feed pre-heat temperature of 1098° C. is required.

Example 1B—Methane Diluent, 950° C. Co-Feed Preheat, 10 Psia Outlet HC Partial Pressure As a comparative to Example 1A, a 575° C. outlet temperature, fluidized bed reactor is simulated with a feed comprising of n-pentane, which is pre-heated to 621° C. prior to feeding into the fluidized bed, and a co-feed comprising of methane and hydrogen, which is separately pre-heated to 950° C. Under these conditions, the catalyst is assumed to have a lights selectivity (C4-products) of ~18%. The residence time within the catalyst bed is assumed to provide for CPD concentration to reach its thermodynamic concentration at the reactor outlet conditions. The hydrogen molar rate in reactor co-feed is set to deliver a molar ratio of hydrogen:n-pentane in feed of 1:1. The methane molar rate in reactor co-feed is set to deliver 100% of the heat of reaction. The combined outlet pressure of all components including hydrogen, with the exception of methane, is set at 10 psia by adjusting the total outlet pressure. To generate 1 lb-mole of CPD in the fluidized bed reactor effluent, it is determined from the simulation that 2.195 lb-moles of n-Pentane and 13.0 lb-moles of methane is required. Additionally, the outlet reactor pressure is determined to be 25 psia. As can be seen by comparing the simulation results of Example 1A and Example 1B, reducing the methane pre-heat temperature from 1098 to 950° C. results in higher methane feed rate (increase from 8.7 to 13.0 lb-mol per lb-mol of CPD produced) in order to provide the same heat of reaction.

Example 1C—Ethane Diluent, 20 Psia Outlet Pressure, 10 Psia HC Partial Pressure

A 20 psia outlet pressure, 575° C. outlet temperature, fluidized bed reactor is simulated with a feed comprising of n-pentane, which is pre-heated to 621° C. prior to feeding into the fluidized bed, and a co-feed comprising of methane and hydrogen, which is separately pre-heated to a temperature required to supply 100% of the heat of reaction. Under these conditions, the catalyst is assumed to have a lights selectivity (C4-products) of ~18%. The residence time within the catalyst bed is assumed to provide for CPD concentration to reach its thermodynamic concentration at the reactor outlet conditions. The hydrogen molar rate in reactor co-feed is set to deliver a molar ratio of hydrogen:n-pentane in feed of 1:1. The ethane molar rate in reactor co-feed is set to deliver an ethane partial pressure at reactor outlet of 10 psia (i.e., combined partial pressure of all other hydrocarbons including hydrogen of 10 psia). Based on the reactor yields, this corresponds to a molar ratio of ethane: n-pentane in feed of about 4:1. To generate 1 lb-mole of CPD in the fluidized bed reactor effluent, it is determined that 2.195 lb-moles of n-Pentane, 8.741 lb-moles of ethane and a co-feed pre-heat temperature of 911° C. is required. As can be seen by comparing the simulation results of Example 1A and Example 1B, use of ethane as co-feed allows for a lower pre-heat temperature owing to its higher heat capacity relative to methane.

Example 1D—Ethane Diluent, 732° C. Co-Feed Preheat, 10 Psia Outlet HC Partial Pressure As a comparative to Example 1C, a 575° C. outlet temperature, fluidized bed reactor is simulated with a feed comprising of n-pentane, which is pre-heated to 621° C. prior to feeding into the fluidized bed, and a co-feed comprising of ethane and hydrogen, which is separately pre-heated to 732° C. Under these conditions, the catalyst is assumed to have a lights selectivity (C4-products) of ~18%. The residence time within the catalyst bed is assumed to provide for CPD concentration to reach its thermodynamic concentration at the reactor outlet conditions. The hydrogen molar rate in reactor co-feed is set to deliver a molar ratio of hydrogen:n-pentane in feed of 1:1. The ethane molar rate in reactor co-feed is set to deliver 100% of the heat of reaction. The combined outlet pressure of all components including hydrogen, with the exception of ethane, is set at 10 psia by adjusting the total outlet pressure. To generate 1 lb-mole of CPD in the fluidized bed reactor effluent, it is determined from the simulation that 2.195 lb-moles of n-Pentane and 19.35 lb-moles of methane is required. Additionally, the outlet reactor pressure is determined to be 33 psia. As can be seen by comparing the simulation results of Example 1D and Example 1C, reducing the ethane pre-heat temperature from 911 to 732° C. results in higher ethane feed rate (increase from 8.7 to 19.4 lb-mol per lb-mol of CPD produced) in order to provide the same heat of reaction.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. For example, the compositions described herein may be free of any component, or composition not expressly recited or disclosed herein. Any method may lack any step not recited or disclosed herein. Likewise, the term "comprising" is considered synonymous with the term "including." And whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for converting acyclic $C_5$ hydrocarbons to cyclic $C_5$ alkenes in a reactor system, wherein the process comprises:

contacting an acyclic $C_5$ feedstock and optionally $H_2$ with a catalyst material comprising a Group 10 metal on any one or more of ZSM-5, zeolite L, and/or silica in at least one reaction zone under reaction conditions to convert at least a portion of the acyclic $C_5$ feedstock to a first effluent comprising cyclic $C_5$ alkenes, wherein the feedstock enters the at least one reaction zone at a temperature of about 300° C. to about 700° C.; and providing a co-feed comprising $H_2$, $C_1$-$C_4$ alkanes and/or $C_1$-$C_4$ alkenes at a temperature of about 600° C. to about 1100° C. to heat the at least one reaction zone, wherein the feedstock and the co-feed are provided to the at least one reaction zone at different locations via different inlets, and wherein the feedstock is heated to a lower temperature than the co-feed.

2. The process of claim 1, wherein the at least one reaction zone is a captive or circulating fluidized bed reactor.

3. The process of claim 1, wherein the first effluent exiting the at least one reaction zone has a temperature of at least about 550° C.

4. The process of claim 1, wherein the reaction conditions comprise a temperature of about 500° C. to about 700° C. and a pressure of about 3 psia to about 100 psia.

5. The process of claim 1, wherein the catalyst material further comprises a binder comprising one or more of silica, titania, zirconia, metal silicates of Group 1 or Group 13 of the Periodic Table, carbides, nitrides, aluminum phosphate, aluminum molybdate, aluminate, surface passivated alumina, and mixtures thereof.

6. The process of claim 1, wherein the feedstock is provided to the at least one reaction zone at a position above where the co-feed is provided.

7. The process of claim 1, further comprising separating catalyst material from the first effluent to produce a separated catalyst material and introducing the separated catalyst material into the at least one reaction zone.

8. The process of claim 1, further comprising transferring at least a portion of the catalyst material to a rejuvenation zone and/or a regeneration zone to produce a rejuvenated catalyst material and/or a regenerated catalyst material; and returning the rejuvenated catalyst material and/or the regenerated catalyst material to the at least one reaction zone.

9. The process of claim 7, further comprising transferring at least a portion of the separated catalyst material to a rejuvenation zone and/or a regeneration zone to produce a rejuvenated catalyst material and/or a regenerated catalyst material; and returning the rejuvenated catalyst material and/or the regenerated catalyst material to the at least one reaction zone.

10. The process of claim 1, further comprising providing fresh catalyst material to the at least one reaction zone.

11. The process of claim 1, further comprising providing heat to the at least one reaction zone via at least one means for heating.

12. The process of claim 1, further comprising separating at least a portion of the co-feed from the first effluent and recycling it back to the at least one reaction zone.

13. The process of claim 1, wherein the co-feed comprises ethane, methane and/or a mixture of ethane and ethylene.

14. The process of claim 1, wherein the acyclic $C_5$ feedstock comprises pentane, pentene, pentadiene or mixtures of two or more thereof, and the cyclic $C_5$ alkenes comprise cyclopentadiene.

15. The process of claim 14, wherein at least about 30 wt % of the acyclic $C_5$ feedstock is converted to cyclopentadiene.

16. The process of claim 14, wherein the co-feed provides at least about 25% of required heat for converting at least a portion of the acyclic $C_5$ feedstock to the first effluent comprising cyclopentadiene.

17. The process of claim 1, wherein the acyclic $C_5$ feedstock consists essentially of pentane, pentene, pentadiene or mixtures of two or more thereof.

18. The process of claim 1, wherein the Group 10 metal is platinum.

19. The process of claim 1, wherein the at least one reaction zone is a fluidized bed.

* * * * *